(12) United States Patent
Edwards et al.

(10) Patent No.: US 9,179,691 B2
(45) Date of Patent: Nov. 10, 2015

(54) DELIVERING AEROSOLIZABLE FOOD PRODUCTS

(75) Inventors: David A. Edwards, Boston, MA (US); Jonathan Man, Bellevue, WA (US); Jonathan Jacques Kamler, Jamaica, NY (US); José Sanchez, Paris (FR)

(73) Assignee: AeroDesigns, Inc., Cambridge, MA (US)

( * ) Notice: Subject to any disclaimer, the term of this patent is extended or adjusted under 35 U.S.C. 154(b) by 697 days.

(21) Appl. No.: 12/747,703

(22) PCT Filed: Oct. 8, 2008

(86) PCT No.: PCT/US2008/079214
§ 371 (c)(1),
(2), (4) Date: Sep. 29, 2010

(87) PCT Pub. No.: WO2009/079078
PCT Pub. Date: Jun. 25, 2009

(65) Prior Publication Data
US 2011/0011394 A1      Jan. 20, 2011

Related U.S. Application Data

(60) Provisional application No. 61/013,861, filed on Dec. 14, 2007, provisional application No. 61/039,783, filed on Mar. 26, 2008.

(51) Int. Cl.
*A61M 11/00* (2006.01)
*A24F 7/00* (2006.01)
(Continued)

(52) U.S. Cl.
CPC ............... *A23G 1/505* (2013.01); *A23G 1/305* (2013.01); *A23G 1/50* (2013.01); *A24F 7/00* (2013.01); *A61M 11/001* (2014.02); *A61M 11/005* (2013.01)

(58) Field of Classification Search
CPC .......... A23G 1/50; A23G 1/305; A23G 1/505; A61M 11/001; A61M 11/005; A24F 7/00
USPC ............. 128/200.14, 200.18, 203.12, 203.23; 426/115; 222/635
See application file for complete search history.

(56) References Cited

U.S. PATENT DOCUMENTS 1,025,440 A * 5/1912 Wittenberg .................... 131/229
1,637,556 A * 8/1927 Denaro ......................... 426/139
(Continued)

FOREIGN PATENT DOCUMENTS

CN         2920281      7/2007
CN       201049059      4/2008
(Continued)

OTHER PUBLICATIONS

International Search Report; PCT/US2008/079214; Y. Lostetter; Apr. 16, 2009.
(Continued)

*Primary Examiner* — Justine Yu
*Assistant Examiner* — Timothy Stanis
(74) *Attorney, Agent, or Firm* — McDermott Will & Emery LLP

(57) ABSTRACT

Aerosolized food products can be of sufficient size to deposit in the mouth without easily entering into the respiratory tract and of small enough size so as to allow for suspension in air. An apparatus incorporating an aerosol generating device and food products can allow for the aerosolization of the food products and the delivery thereof in a matter suitable for inhalation or deposition and subsequent ingestion. The food delivery apparatus represents a novel manner of delivering food to the mouths of humans and animals. Indeed, the apparatus of the invention is designed to produce, transport, and direct aerosolized food particles of sufficient size to deposit in the mouth without substantial exposure or entry into the respiratory tract and of small enough size so as to allow for suspension in air.

41 Claims, 25 Drawing Sheets

(51) Int. Cl.
  *A23G 1/50* (2006.01)
  *A23G 1/30* (2006.01)

(56) References Cited

U.S. PATENT DOCUMENTS

| | | | |
|---|---|---|---|
| 1,936,835 A * | 11/1933 | William | 426/138 |
| 2,539,061 A * | 1/1951 | Coles | 239/467 |
| 3,771,535 A * | 11/1973 | Mezoff | 131/187 |
| 3,811,620 A * | 5/1974 | Gebhardt | 239/499 |
| 4,624,414 A * | 11/1986 | Ferrazza | 239/467 |
| 4,907,581 A | 3/1990 | King | |
| 4,940,051 A | 7/1990 | Lankinen | |
| 4,951,659 A | 8/1990 | Weiler et al. | |
| 5,002,048 A | 3/1991 | Makiej, Jr. | |
| 5,020,530 A | 6/1991 | Miller | |
| 5,056,511 A | 10/1991 | Ronge | |
| 5,074,294 A | 12/1991 | Chiesi | |
| 5,099,833 A | 3/1992 | Michaels | |
| 5,101,838 A | 4/1992 | Schwartz et al. | |
| 5,119,806 A | 6/1992 | Palson et al. | |
| 5,139,016 A | 8/1992 | Waser | |
| 5,186,164 A | 2/1993 | Raghuprasad | |
| 5,239,991 A | 8/1993 | Chawla et al. | |
| 5,243,970 A | 9/1993 | Ambrosio et al. | |
| 5,263,475 A | 11/1993 | Altermatt et al. | |
| 5,267,555 A | 12/1993 | Pajalich | |
| 5,273,531 A * | 12/1993 | Knoepfler | 604/58 |
| 5,287,850 A | 2/1994 | Haber et al. | |
| 5,297,542 A | 3/1994 | Bacon | |
| 5,320,714 A | 6/1994 | Brendel | |
| 5,331,953 A | 7/1994 | Andersson et al. | |
| 5,347,998 A | 9/1994 | Hodson et al. | |
| 5,355,873 A | 10/1994 | Del Bon et al. | |
| 5,385,140 A | 1/1995 | Smith | |
| 5,386,825 A | 2/1995 | Bates | |
| 5,415,162 A | 5/1995 | Casper et al. | |
| 5,437,271 A | 8/1995 | Hodson et al. | |
| 5,476,093 A | 12/1995 | Lankinen | |
| 5,479,920 A | 1/1996 | Piper et al. | |
| 5,490,497 A | 2/1996 | Chippendale et al. | |
| 5,490,630 A | 2/1996 | Hecker | |
| 5,505,195 A | 4/1996 | Wolf et al. | |
| 5,524,613 A | 6/1996 | Haber et al. | |
| 5,533,502 A | 7/1996 | Piper | |
| 5,568,807 A | 10/1996 | Mecikalski | |
| 5,582,162 A | 12/1996 | Petersson | |
| 5,595,175 A | 1/1997 | Malcher et al. | |
| 5,615,670 A | 4/1997 | Rhodes | |
| 5,617,845 A | 4/1997 | Poss et al. | |
| RE35,552 E | 7/1997 | Lankinen | |
| 5,642,727 A | 7/1997 | Datta et al. | |
| 5,669,378 A | 9/1997 | Pera et al. | |
| 5,670,167 A | 9/1997 | Sleath et al. | |
| 5,676,130 A | 10/1997 | Gupte et al. | |
| 5,678,538 A | 10/1997 | Drought | |
| 5,682,875 A | 11/1997 | Blower et al. | |
| 5,685,294 A | 11/1997 | Gupte et al. | |
| 5,694,920 A | 12/1997 | Abrams et al. | |
| 5,724,962 A | 3/1998 | Vidgrén et al. | |
| 5,724,986 A | 3/1998 | Jones, Jr. et al. | |
| 5,746,227 A * | 5/1998 | Rose et al. | 131/270 |
| 5,797,392 A | 8/1998 | Keldmann et al. | |
| 5,819,756 A | 10/1998 | Mielordt | |
| 5,839,430 A | 11/1998 | Cama | |
| 5,842,468 A | 12/1998 | Denyer et al. | |
| 5,848,587 A | 12/1998 | King | |
| 5,855,202 A | 1/1999 | Andrade | |
| 5,873,359 A | 2/1999 | Zapol et al. | |
| 5,881,721 A | 3/1999 | Bunce et al. | |
| 5,893,371 A | 4/1999 | Rose et al. | |
| 5,894,841 A | 4/1999 | Voges | |
| 5,918,594 A | 7/1999 | Asking et al. | |
| 5,947,117 A | 9/1999 | Herold et al. | |
| 5,954,047 A | 9/1999 | Armer et al. | |
| 5,955,439 A | 9/1999 | Green | |
| 5,983,893 A | 11/1999 | Wetterlin | |
| 6,000,394 A | 12/1999 | Blaha-Schnabel et al. | |
| 6,055,980 A | 5/2000 | Mecikalski et al. | |
| 6,056,169 A | 5/2000 | Bruna et al. | |
| 6,067,984 A | 5/2000 | Piper | |
| 6,076,520 A | 6/2000 | Cooper | |
| 6,085,741 A | 7/2000 | Becker | |
| 6,098,619 A | 8/2000 | Britto et al. | |
| 6,102,035 A | 8/2000 | Asking et al. | |
| 6,102,179 A | 8/2000 | Hodson et al. | |
| 6,119,684 A | 9/2000 | Nöhl et al. | |
| 6,138,673 A | 10/2000 | Shepherd | |
| 6,142,145 A | 11/2000 | Dagsland et al. | |
| 6,142,339 A | 11/2000 | Blacker et al. | |
| 6,148,815 A | 11/2000 | Wolf | |
| 6,152,130 A | 11/2000 | Abrams et al. | |
| 6,176,442 B1 | 1/2001 | Eicher et al. | |
| 6,230,707 B1 | 5/2001 | Hörlin | |
| 6,234,169 B1 | 5/2001 | Bulbrook et al. | |
| 6,237,591 B1 | 5/2001 | Jackson | |
| 6,250,301 B1 | 6/2001 | Pate | |
| 6,260,549 B1 | 7/2001 | Sosiak | |
| 6,285,731 B1 | 9/2001 | Marnfeldt et al. | |
| 6,286,506 B1 | 9/2001 | MacAndrew et al. | |
| 6,306,440 B1 | 10/2001 | Bäckstrom et al. | |
| 6,328,032 B1 | 12/2001 | Virtanen | |
| 6,328,033 B1 | 12/2001 | Avrahami | |
| 6,332,461 B1 | 12/2001 | Hyppölä | |
| 6,347,629 B1 | 2/2002 | Braithwaite | |
| 6,390,090 B1 | 5/2002 | Piper | |
| 6,418,926 B1 | 7/2002 | Chawla | |
| 6,422,236 B1 | 7/2002 | Nilsson et al. | |
| 6,427,683 B1 | 8/2002 | Drachmann et al. | |
| 6,435,177 B1 * | 8/2002 | Schmidt et al. | 128/200.23 |
| 6,439,227 B1 | 8/2002 | Myrman et al. | |
| 6,443,151 B1 | 9/2002 | Ruskewicz | |
| 6,453,900 B1 | 9/2002 | Barnes, Jr. et al. | |
| 6,527,151 B1 | 3/2003 | Pavkov et al. | |
| 6,557,550 B1 | 5/2003 | Clarke | |
| 6,571,793 B1 | 6/2003 | Nilsson | |
| 6,575,160 B1 | 6/2003 | Volgyesi | |
| 6,581,590 B1 | 6/2003 | Genova et al. | |
| 6,595,204 B2 | 7/2003 | Genova et al. | |
| 6,595,206 B2 | 7/2003 | Vito | |
| 6,604,522 B2 | 8/2003 | Arvidsson et al. | |
| 6,606,990 B2 | 8/2003 | Stapleton et al. | |
| 6,606,992 B1 | 8/2003 | Schuler et al. | |
| 6,615,827 B2 | 9/2003 | Greenwood et al. | |
| 6,634,360 B1 | 10/2003 | Flodin | |
| 6,637,431 B2 | 10/2003 | Ekelius et al. | |
| 6,640,050 B2 | 10/2003 | Nichols et al. | |
| 6,651,651 B1 | 11/2003 | Bonney et al. | |
| 6,668,826 B1 | 12/2003 | Myrman | |
| 6,679,252 B2 | 1/2004 | Sladek | |
| 6,681,763 B2 | 1/2004 | Ferris | |
| 6,681,768 B2 | 1/2004 | Haaije de Boer et al. | |
| 6,681,769 B2 | 1/2004 | Sprinkel, Jr. et al. | |
| 6,701,922 B2 | 3/2004 | Hindle et al. | |
| 6,715,487 B2 | 4/2004 | Nichols et al. | |
| 6,729,328 B2 | 5/2004 | Goldemann | |
| 6,740,884 B2 | 5/2004 | Lee et al. | |
| 6,752,147 B1 | 6/2004 | Goldemann et al. | |
| 6,752,153 B1 | 6/2004 | Eckert | |
| 6,779,520 B2 | 8/2004 | Genova et al. | |
| 6,800,643 B2 | 10/2004 | Cuenoud et al. | |
| 6,810,873 B1 | 11/2004 | Haikarainen et al. | |
| 6,810,874 B1 | 11/2004 | Koskela et al. | |
| 6,810,875 B2 | 11/2004 | Staniforth et al. | |
| 6,814,072 B1 | 11/2004 | Seppälä | |
| 6,824,080 B2 | 11/2004 | Matsugi et al. | |
| 6,845,770 B2 | 1/2005 | Klimowicz et al. | |
| 6,845,772 B2 | 1/2005 | Braithwaite et al. | |
| 6,854,461 B2 | 2/2005 | Nichols et al. | |
| 6,857,427 B2 | 2/2005 | Ziegler et al. | |
| 6,881,398 B2 | 4/2005 | Myrman et al. | |
| 6,886,560 B1 | 5/2005 | Seppälä | |
| 6,904,907 B2 | 6/2005 | Speldrich et al. | |
| 6,907,880 B1 | 6/2005 | Heckenmüller et al. | |
| 6,915,802 B1 | 7/2005 | Anderson et al. | |

(56) References Cited

U.S. PATENT DOCUMENTS

| | | |
|---|---|---|
| 6,926,003 B2 | 8/2005 | Seppälä |
| 6,929,004 B1 | 8/2005 | Bonney et al. |
| 6,981,660 B2 | 1/2006 | Piper |
| 6,983,748 B2 | 1/2006 | Brown et al. |
| 6,990,975 B1 | 1/2006 | Jones et al. |
| 7,013,888 B2 | 3/2006 | Hughes et al. |
| 7,025,058 B2 | 4/2006 | Armstrong et al. |
| 7,025,059 B2 | 4/2006 | Pera |
| 7,032,593 B2 | 4/2006 | Johnston et al. |
| 7,032,594 B2 | 4/2006 | Newton et al. |
| 7,040,314 B2 | 5/2006 | Nguyen et al. |
| 7,056,494 B2 | 6/2006 | Adjei et al. |
| 7,117,867 B2 | 10/2006 | Cox et al. |
| 7,128,067 B2 | 10/2006 | Byron et al. |
| 7,131,440 B2 | 11/2006 | Sonntag |
| 7,131,441 B1 | 11/2006 | Keller et al. |
| 7,143,765 B2 | 12/2006 | Asking et al. |
| 7,146,978 B2 | 12/2006 | Edwards et al. |
| 7,147,170 B2 | 12/2006 | Nguyen |
| 7,173,222 B2 | 2/2007 | Cox et al. |
| 7,174,890 B2 | 2/2007 | Goldemann |
| 7,185,651 B2 | 3/2007 | Alston et al. |
| 7,217,733 B2 | 5/2007 | Almirante et al. |
| 7,228,830 B2 | 6/2007 | Watanabe |
| 7,234,459 B2 | 6/2007 | Del Bon |
| 7,243,648 B2 | 7/2007 | Yang et al. |
| 7,249,600 B2 | 7/2007 | Chawla |
| 7,267,813 B2 | 9/2007 | Watanbe et al. |
| 7,275,538 B2 | 10/2007 | Nakamura et al. |
| 7,278,426 B2 | 10/2007 | Myrman |
| 7,281,539 B2 | 10/2007 | Chawla |
| 7,284,553 B2 | 10/2007 | Hochrainer |
| 7,322,352 B2 | 1/2008 | Minshull et al. |
| 7,373,938 B2 | 5/2008 | Nichols et al. |
| 7,383,837 B2 | 6/2008 | Robertson et al. |
| 7,400,940 B2 | 7/2008 | McRae et al. |
| 7,404,400 B2 | 7/2008 | Lulla et al. |
| 7,418,962 B1 | 9/2008 | Rao |
| 7,424,888 B2 | 9/2008 | Harvey et al. |
| 7,431,916 B2 | 10/2008 | Nilsson et al. |
| 7,434,579 B2 | 10/2008 | Young et al. |
| 7,451,761 B2 | 11/2008 | Hickey et al. |
| 7,458,373 B2 | 12/2008 | Nichols et al. |
| 7,461,649 B2 | 12/2008 | Gamard et al. |
| 7,464,706 B2 | 12/2008 | Steiner et al. |
| 7,520,278 B2 | 4/2009 | Crowder et al. |
| 7,540,282 B2 | 6/2009 | O'Leary |
| 7,552,728 B2 | 6/2009 | Bonney et al. |
| 7,571,722 B2 | 8/2009 | Wuttke et al. |
| 7,581,540 B2 | 9/2009 | Hale et al. |
| 7,594,507 B2 | 9/2009 | Davis |
| 7,597,099 B2 | 10/2009 | Jones et al. |
| 7,604,006 B2 | 10/2009 | Wolf et al. |
| 7,617,822 B2 | 11/2009 | De Boer et al. |
| 7,621,266 B2 | 11/2009 | Kladders et al. |
| 7,624,733 B2 | 12/2009 | Riley et al. |
| 7,647,928 B2 | 1/2010 | Muellinger et al. |
| 7,665,460 B2 | 2/2010 | Lindsay et al. |
| 7,669,596 B2 | 3/2010 | Alston |
| 7,677,467 B2 | 3/2010 | Fink et al. |
| 7,681,569 B2 | 3/2010 | Rock |
| 7,683,029 B2 | 3/2010 | Hindle et al. |
| 7,699,052 B2 | 4/2010 | Schiewe et al. |
| 7,708,011 B2 | 5/2010 | Hochrainer et al. |
| 7,708,014 B2 | 5/2010 | Yamashita et al. |
| 7,726,310 B2 | 6/2010 | Andrus et al. |
| 7,735,485 B2 | 6/2010 | Yamashita et al. |
| 7,748,378 B2 | 7/2010 | Hodson |
| 7,748,382 B2 | 7/2010 | Denyer et al. |
| 7,766,012 B2 | 8/2010 | Scheuch et al. |
| 7,766,019 B2 | 8/2010 | Luzenberg, Jr. |
| 7,779,838 B2 | 8/2010 | Hetzer et al. |
| 7,779,839 B2 | 8/2010 | Pocock et al. |
| 7,802,569 B2 | 9/2010 | Yeates et al. |
| 7,802,570 B2 | 9/2010 | Mecikalski |
| 7,810,494 B2 | 10/2010 | Harmer et al. |
| 7,827,989 B2 | 11/2010 | Butterworth et al. |
| 7,832,393 B2 | 11/2010 | Vito |
| 7,832,394 B2 | 11/2010 | Schechter et al. |
| 7,841,338 B2 | 11/2010 | Dunne et al. |
| 7,841,340 B2 | 11/2010 | Andersson et al. |
| 7,845,346 B2 | 12/2010 | Langford et al. |
| 7,845,349 B2 | 12/2010 | Eason et al. |
| 7,850,663 B2 | 12/2010 | Sullivan et al. |
| 7,854,225 B2 | 12/2010 | Pasbrig et al. |
| 7,861,713 B2 | 1/2011 | Dhuper et al. |
| 2002/0017296 A1 | 2/2002 | Hickle |
| 2002/0020408 A1 | 2/2002 | Knauer |
| 2002/0040713 A1 | 4/2002 | Eisele et al. |
| 2002/0076382 A1 | 6/2002 | Kaplan et al. |
| 2002/0090601 A1 | 7/2002 | Strupat et al. |
| 2002/0099033 A1 | 7/2002 | Meyer et al. |
| 2002/0112724 A1 | 8/2002 | Newhouse et al. |
| 2002/0155066 A1 | 10/2002 | Placke et al. |
| 2002/0165482 A1 | 11/2002 | Keldmann et al. |
| 2002/0189615 A1 | 12/2002 | Henry et al. |
| 2003/0106555 A1 | 6/2003 | Tovey |
| 2003/0164169 A1 | 9/2003 | Stangl et al. |
| 2003/0185762 A1 | 10/2003 | Cowan et al. |
| 2003/0192538 A1 | 10/2003 | Myrman |
| 2003/0196654 A1 | 10/2003 | Stein |
| 2004/0016429 A1 | 1/2004 | Bocquee |
| 2004/0031484 A1 | 2/2004 | Halamish |
| 2004/0050385 A1 | 3/2004 | Bonney et al. |
| 2004/0050965 A1 | 3/2004 | Chien |
| 2004/0065324 A1 | 4/2004 | Pivinski |
| 2004/0079368 A1 | 4/2004 | Gupta et al. |
| 2004/0099266 A1 | 5/2004 | Cross et al. |
| 2004/0102434 A1 | 5/2004 | Hale et al. |
| 2004/0159322 A1 | 8/2004 | Kladders et al. |
| 2004/0173211 A1 | 9/2004 | Kladders et al. |
| 2004/0177848 A1 | 9/2004 | Alley |
| 2004/0187864 A1 | 9/2004 | Adams |
| 2004/0191176 A1 | 9/2004 | Kaplan |
| 2004/0221840 A1 | 11/2004 | Stockman-Lamb |
| 2004/0223916 A1 | 11/2004 | Burt et al. |
| 2004/0231666 A1 | 11/2004 | Barker et al. |
| 2004/0235807 A1 | 11/2004 | Weinrich et al. |
| 2004/0236282 A1 | 11/2004 | Braithwaite |
| 2005/0005933 A1 | 1/2005 | Seppala |
| 2005/0048127 A1 | 3/2005 | Brown et al. |
| 2005/0051161 A1 | 3/2005 | Anandampillai et al. |
| 2005/0053665 A1 | 3/2005 | Ek et al. |
| 2005/0056275 A1 | 3/2005 | Ingle et al. |
| 2005/0092323 A1 | 5/2005 | Frietsch et al. |
| 2005/0126562 A1 | 6/2005 | Rabinowitz et al. |
| 2005/0129833 A1* | 6/2005 | Kincaid et al. ................ 426/631 |
| 2005/0161467 A1 | 7/2005 | Jones |
| 2005/0172962 A1 | 8/2005 | Gumaste et al. |
| 2005/0172963 A1 | 8/2005 | Allan et al. |
| 2005/0183725 A1 | 8/2005 | Gumaste et al. |
| 2005/0236501 A1 | 10/2005 | Zimlich, Jr. et al. |
| 2005/0251289 A1 | 11/2005 | Bonney et al. |
| 2005/0252510 A1 | 11/2005 | Young et al. |
| 2005/0257793 A1 | 11/2005 | Tatsumoto |
| 2005/0263151 A1 | 12/2005 | Hochrainer et al. |
| 2005/0268911 A1 | 12/2005 | Cross et al. |
| 2005/0274378 A1 | 12/2005 | Bonney et al. |
| 2005/0277688 A1 | 12/2005 | Li et al. |
| 2006/0030550 A1 | 2/2006 | Lithgow et al. |
| 2006/0037612 A1 | 2/2006 | Herder et al. |
| 2006/0048772 A1 | 3/2006 | Borgschulte |
| 2006/0057106 A1 | 3/2006 | Yamashita et al. |
| 2006/0102178 A1 | 5/2006 | Feiner et al. |
| 2006/0147520 A1 | 7/2006 | Ruegg |
| 2006/0177468 A1 | 8/2006 | Katsikis et al. |
| 2006/0191931 A1 | 8/2006 | Rand |
| 2006/0205949 A1 | 9/2006 | Dalziel et al. |
| 2006/0207591 A1 | 9/2006 | Gallem et al. |
| 2006/0213503 A1 | 9/2006 | Borgschulte et al. |
| 2006/0276523 A1 | 12/2006 | Almirante et al. |
| 2006/0283447 A1 | 12/2006 | Dhuper et al. |
| 2006/0292082 A1 | 12/2006 | Sarkar et al. |
| 2007/0009445 A1 | 1/2007 | Eck |

(56) References Cited

U.S. PATENT DOCUMENTS

| | | |
|---|---|---|
| 2007/0012316 A1 | 1/2007 | Truza |
| 2007/0020190 A1 | 1/2007 | Razzetti et al. |
| 2007/0023042 A1 | 2/2007 | Lee |
| 2007/0023043 A1 | 2/2007 | Von Hollen et al. |
| 2007/0039618 A1 | 2/2007 | Braithwaite |
| 2007/0041994 A1 | 2/2007 | McDowell, Jr. |
| 2007/0044793 A1 | 3/2007 | Kleinstreuer et al. |
| 2007/0062548 A1 | 3/2007 | Horstmann et al. |
| 2007/0068524 A1 | 3/2007 | Nilsson et al. |
| 2007/0099454 A1 | 5/2007 | Gordon |
| 2007/0110678 A1 | 5/2007 | Zierenberg et al. |
| 2007/0125370 A1 | 6/2007 | Denyer et al. |
| 2007/0125375 A1 | 6/2007 | Finlay et al. |
| 2007/0128124 A1 | 6/2007 | Kraus et al. |
| 2007/0131225 A1 | 6/2007 | Rand |
| 2007/0163574 A1 | 7/2007 | Rohrschneider et al. |
| 2007/0163582 A1 | 7/2007 | Rand |
| 2007/0181124 A1 | 8/2007 | Casper et al. |
| 2007/0190163 A1 | 8/2007 | Malaknov et al. |
| 2007/0204864 A1 | 9/2007 | Grychowski et al. |
| 2007/0209661 A1 | 9/2007 | Smyth et al. |
| 2007/0215149 A1 | 9/2007 | King et al. |
| 2007/0221218 A1 | 9/2007 | Warden et al. |
| 2007/0224220 A1 | 9/2007 | Kersten et al. |
| 2007/0240709 A1 | 10/2007 | Woolley et al. |
| 2007/0240712 A1 | 10/2007 | Fleming et al. |
| 2007/0240713 A1 | 10/2007 | Boeck |
| 2007/0251524 A1 | 11/2007 | Harmer et al. |
| 2007/0256688 A1 | 11/2007 | Schuster et al. |
| 2007/0267016 A1 | 11/2007 | Thoemmes et al. |
| 2007/0267032 A1 | 11/2007 | Shan |
| 2007/0272235 A1 | 11/2007 | Miyamoto |
| 2007/0272763 A1 | 11/2007 | Dunne et al. |
| 2007/0283954 A1 | 12/2007 | Dhuper et al. |
| 2007/0286818 A1 | 12/2007 | Tatapudy et al. |
| 2007/0287753 A1 | 12/2007 | Charney et al. |
| 2007/0289590 A1 | 12/2007 | Kreutzmann et al. |
| 2007/0295332 A1 | 12/2007 | Ziegler et al. |
| 2007/0295333 A1 | 12/2007 | Fourment et al. |
| 2007/0298112 A1 | 12/2007 | Axt et al. |
| 2008/0001009 A1 | 1/2008 | Young |
| 2008/0017189 A1 | 1/2008 | Ruckdeschel et al. |
| 2008/0017198 A1 | 1/2008 | Ivri |
| 2008/0038207 A1 | 2/2008 | Edwards et al. |
| 2008/0041372 A1 | 2/2008 | Poole et al. |
| 2008/0048054 A1 | 2/2008 | Peters et al. |
| 2008/0066743 A1 | 3/2008 | Grychowski et al. |
| 2008/0092885 A1 | 4/2008 | Von Schuckmann |
| 2008/0092887 A1 | 4/2008 | Hodson et al. |
| 2008/0092888 A1 | 4/2008 | Haroutunian |
| 2008/0099016 A1 | 5/2008 | Pocock et al. |
| 2008/0110462 A1 | 5/2008 | Chekal et al. |
| 2008/0116220 A1 | 5/2008 | Pocock et al. |
| 2008/0121228 A1 | 5/2008 | Smyth et al. |
| 2008/0127968 A1 | 6/2008 | Somaraju et al. |
| 2008/0127972 A1 | 6/2008 | Morton |
| 2008/0135047 A1 | 6/2008 | Johnson et al. |
| 2008/0142008 A1 | 6/2008 | Pocock et al. |
| 2008/0163868 A1 | 7/2008 | Pocock et al. |
| 2008/0184998 A1 | 8/2008 | Myrman et al. |
| 2008/0185000 A1 | 8/2008 | Von Schuckmann |
| 2008/0190420 A1 | 8/2008 | Lev |
| 2008/0190424 A1 | 8/2008 | Lucking et al. |
| 2008/0196718 A1 | 8/2008 | Connell et al. |
| 2008/0199161 A1 | 8/2008 | Hickey et al. |
| 2008/0202515 A1 | 8/2008 | Hodson et al. |
| 2008/0221029 A1 | 9/2008 | Day |
| 2008/0223365 A1 | 9/2008 | Von Schuckmann |
| 2008/0223366 A1 | 9/2008 | Davies et al. |
| 2008/0226736 A1 | 9/2008 | Caponetti et al. |
| 2008/0230052 A1 | 9/2008 | Montaser |
| 2008/0236579 A1 | 10/2008 | Zierenberg |
| 2008/0241255 A1 | 10/2008 | Rose et al. |
| 2008/0245363 A1 | 10/2008 | Korevaar et al. |
| 2008/0251072 A1 | 10/2008 | Lulla et al. |
| 2008/0257338 A1 | 10/2008 | Gee-Turner |
| 2008/0274189 A1 | 11/2008 | Collingwood et al. |
| 2008/0279948 A1 | 11/2008 | Collingwood et al. |
| 2008/0280828 A1 | 11/2008 | Wang et al. |
| 2008/0283054 A1 | 11/2008 | Rohrschneider et al. |
| 2008/0283055 A1 | 11/2008 | Rohrschneider et al. |
| 2008/0283056 A1 | 11/2008 | Rohrschneider et al. |
| 2008/0283057 A1 | 11/2008 | Rohrschneider et al. |
| 2008/0289626 A1 | 11/2008 | Rohrschneider et al. |
| 2008/0289627 A1 | 11/2008 | Rohrschneider et al. |
| 2008/0295832 A1 | 12/2008 | Geser et al. |
| 2008/0295833 A1 | 12/2008 | Rohrschneider et al. |
| 2008/0299049 A1 | 12/2008 | Stangl |
| 2008/0308095 A1 | 12/2008 | Trees et al. |
| 2008/0308096 A1 | 12/2008 | Borgschulte et al. |
| 2008/0308102 A1 | 12/2008 | Davies et al. |
| 2008/0311111 A1 | 12/2008 | Drew et al. |
| 2008/0314380 A1 | 12/2008 | Watchtel et al. |
| 2008/0314383 A1 | 12/2008 | Barney et al. |
| 2008/0314384 A1 | 12/2008 | Harris et al. |
| 2008/0315829 A1 | 12/2008 | Jones et al. |
| 2009/0005423 A1 | 1/2009 | Gonda |
| 2009/0007909 A1 | 1/2009 | Carrico |
| 2009/0013993 A1 | 1/2009 | Bird et al. |
| 2009/0025714 A1 | 1/2009 | Denyer et al. |
| 2009/0025718 A1 | 1/2009 | Denyer et al. |
| 2009/0025720 A1 | 1/2009 | Chen |
| 2009/0025721 A1 | 1/2009 | Ellwanger et al. |
| 2009/0025722 A1 | 1/2009 | Pieper et al. |
| 2009/0028800 A1 | 1/2009 | Peeples et al. |
| 2009/0032019 A1 | 2/2009 | Green et al. |
| 2009/0050138 A1 | 2/2009 | Hamaguchi et al. |
| 2009/0050149 A1 | 2/2009 | Von Schuckmann |
| 2009/0056708 A1 | 3/2009 | Stenzler et al. |
| 2009/0064996 A1 | 3/2009 | Rosh |
| 2009/0064997 A1 | 3/2009 | Li |
| 2009/0084379 A1 | 4/2009 | Goeckner et al. |
| 2009/0090360 A1 | 4/2009 | Pocock et al. |
| 2009/0107495 A1 | 4/2009 | Ni et al. |
| 2009/0110679 A1 | 4/2009 | Li et al. |
| 2009/0114219 A1 | 5/2009 | Ferris et al. |
| 2009/0120431 A1 | 5/2009 | Borgschulte et al. |
| 2009/0123548 A1 | 5/2009 | Tom |
| 2009/0126723 A1 | 5/2009 | Dhuper et al. |
| 2009/0139517 A1 | 6/2009 | Wachtel et al. |
| 2009/0145433 A1 | 6/2009 | James |
| 2009/0151717 A1 | 6/2009 | Bowen et al. |
| 2009/0159080 A1 | 6/2009 | Giroux |
| 2009/0165788 A1 | 7/2009 | Warden et al. |
| 2009/0165791 A1 | 7/2009 | Wendland |
| 2009/0170903 A1 | 7/2009 | Armani et al. |
| 2009/0173341 A1 | 7/2009 | Reinhold et al. |
| 2009/0173345 A1 | 7/2009 | Wachtel et al. |
| 2009/0178672 A1 | 7/2009 | Mullinger et al. |
| 2009/0178676 A1 | 7/2009 | Villax et al. |
| 2009/0181935 A1 | 7/2009 | Villetti et al. |
| 2009/0188490 A1 | 7/2009 | Han |
| 2009/0205657 A1 | 8/2009 | Barney et al. |
| 2009/0217923 A1 | 9/2009 | Boehm et al. |
| 2009/0223516 A1 | 9/2009 | Connelly et al. |
| 2009/0223517 A1 | 9/2009 | Barney et al. |
| 2009/0235930 A1 | 9/2009 | Young et al. |
| 2009/0235931 A1 | 9/2009 | Young et al. |
| 2009/0241949 A1 | 10/2009 | Smutney et al. |
| 2009/0250056 A1 | 10/2009 | Pentagragas |
| 2009/0250058 A1 | 10/2009 | Lastow et al. |
| 2009/0258046 A1 | 10/2009 | Nyce |
| 2009/0270752 A1 | 10/2009 | Coifman |
| 2009/0277446 A1 | 11/2009 | Walz |
| 2009/0293874 A1 | 12/2009 | Braithwaite |
| 2009/0308388 A1 | 12/2009 | Chawla |
| 2009/0308391 A1 | 12/2009 | Smutney et al. |
| 2009/0308772 A1 | 12/2009 | Abrams |
| 2009/0311314 A1 | 12/2009 | Hartig et al. |
| 2009/0314287 A1 | 12/2009 | Spallek et al. |
| 2009/0314291 A1 | 12/2009 | Anderson et al. |
| 2009/0314292 A1 | 12/2009 | Overfield et al. |
| 2009/0320837 A1 | 12/2009 | Smith et al. |
| 2010/0000523 A1 | 1/2010 | Rosh |

(56) References Cited

U.S. PATENT DOCUMENTS

| | | |
|---|---|---|
| 2010/0000530 A1 | 1/2010 | Jauernig et al. |
| 2010/0000531 A1 | 1/2010 | Smith et al. |
| 2010/0006096 A1 | 1/2010 | Kakade |
| 2010/0012115 A1 | 1/2010 | Bacon |
| 2010/0012119 A1 | 1/2010 | Sallak et al. |
| 2010/0012120 A1 | 1/2010 | Herder et al. |
| 2010/0018527 A1 | 1/2010 | Papet et al. |
| 2010/0024815 A1 | 2/2010 | Kladders |
| 2010/0035922 A1 | 2/2010 | Amari et al. |
| 2010/0051027 A1 | 3/2010 | Remmelgas et al. |
| 2010/0059049 A1 | 3/2010 | Genosar |
| 2010/0059050 A1 | 3/2010 | Wachtel |
| 2010/0065048 A1 | 3/2010 | Mueller-Walz et al. |
| 2010/0065739 A1 | 3/2010 | Chambers et al. |
| 2010/0078022 A1 | 4/2010 | Striebig et al. |
| 2010/0083959 A1 | 4/2010 | Siller |
| 2010/0104515 A1 | 4/2010 | Knox |
| 2010/0108058 A1 | 5/2010 | Glusker et al. |
| 2010/0116271 A1 | 5/2010 | Horsford |
| 2010/0132699 A1 | 6/2010 | Burolla et al. |
| 2010/0139652 A1 | 6/2010 | Lipp et al. |
| 2010/0139654 A1 | 6/2010 | Thoemmes et al. |
| 2010/0139655 A1 | 6/2010 | Genosar et al. |
| 2010/0147292 A1 | 6/2010 | Hamaguchi et al. |
| 2010/0154795 A1 | 6/2010 | Pentafragas |
| 2010/0163042 A1 | 7/2010 | Bhowmick et al. |
| 2010/0175697 A1 | 7/2010 | Massot |
| 2010/0175698 A1 | 7/2010 | Rand |
| 2010/0186740 A1 | 7/2010 | Lewis et al. |
| 2010/0192945 A1 | 8/2010 | Cook et al. |
| 2010/0192946 A1 | 8/2010 | Oi et al. |
| 2010/0192949 A1 | 8/2010 | Wright et al. |
| 2010/0192950 A1 | 8/2010 | Chopard |
| 2010/0196483 A1 | 8/2010 | Muellinger et al. |
| 2010/0199986 A1 | 8/2010 | Von Brunn |
| 2010/0204602 A1 | 8/2010 | Addington et al. |
| 2010/0229856 A1 | 9/2010 | Von Brunn |
| 2010/0236546 A1 | 9/2010 | Yamada et al. |
| 2010/0242955 A1 | 9/2010 | Hansen |
| 2010/0242956 A1 | 9/2010 | Yamada et al. |
| 2010/0242960 A1 | 9/2010 | Zangerle |
| 2010/0249584 A1 | 9/2010 | Albertelli |
| 2010/0252032 A1 | 10/2010 | Thoemmes et al. |
| 2010/0258118 A1 | 10/2010 | Morton |
| 2010/0258119 A1 | 10/2010 | Dams |
| 2010/0263667 A1 | 10/2010 | Jinks et al. |
| 2010/0275912 A1 | 11/2010 | Lulla et al. |
| 2010/0288277 A1 | 11/2010 | Gordon et al. |
| 2010/0291221 A1 | 11/2010 | Cook et al. |
| 2010/0294278 A1 | 11/2010 | Mosier et al. |
| 2010/0300433 A1 | 12/2010 | Sharma et al. |
| 2010/0300439 A1 | 12/2010 | Djupesland et al. |
| 2010/0300440 A1 | 12/2010 | Deboeck et al. |
| 2010/0300442 A1 | 12/2010 | Houzego et al. |
| 2010/0305547 A1 | 12/2010 | Franco |
| 2010/0307487 A1 | 12/2010 | Dunsmore et al. |
| 2010/0307491 A1 | 12/2010 | Lastow |
| 2010/0307492 A1 | 12/2010 | Fabien |
| 2010/0307494 A1 | 12/2010 | Thoemmes et al. |
| 2010/0314462 A1 | 12/2010 | Mather et al. |
| 2010/0316576 A1 | 12/2010 | Keller et al. |
| 2010/0319686 A1 | 12/2010 | Schennum |
| 2010/0319694 A1 | 12/2010 | Cook et al. |

FOREIGN PATENT DOCUMENTS

| | | |
|---|---|---|
| CN | 201049129 | 4/2008 |
| CN | 101300041 | 11/2008 |
| CN | 201161038 | 12/2008 |
| CN | 201197840 | 2/2009 |
| CN | 101415457 | 4/2009 |
| CN | 201453796 | 5/2010 |
| CN | 101856531 | 10/2010 |
| CN | 101884818 | 11/2010 |
| CN | 101918144 | 12/2010 |
| EP | 0 262 239 | 4/1988 |
| EP | 0 311 770 | 4/1989 |
| EP | 0 258 238 | 6/1990 |
| EP | 0 481 666 | 10/1991 |
| EP | 0 237 507 | 12/1991 |
| EP | 0 520 440 | 6/1992 |
| EP | 0 516 510 | 12/1992 |
| EP | 0 547 429 | 6/1993 |
| EP | 0 424 790 | 8/1993 |
| EP | 0 441 643 | 12/1993 |
| EP | 0 363 060 | 4/1994 |
| EP | 0 475 257 | 6/1994 |
| EP | 0 601 036 | 6/1994 |
| EP | 0 611 577 | 8/1994 |
| EP | 0 407 028 | 9/1994 |
| EP | 0 626 180 | 11/1994 |
| EP | 0 633 792 | 1/1995 |
| EP | 0 661 070 | 7/1995 |
| EP | 0 667 793 | 8/1995 |
| EP | 0 682 955 | 11/1995 |
| EP | 0 684 851 | 12/1995 |
| EP | 0 619 746 | 4/1996 |
| EP | 0 707 862 | 4/1996 |
| EP | 0 714 243 | 6/1996 |
| EP | 0 557 333 | 9/1996 |
| EP | 0 563 131 | 9/1996 |
| EP | 0 561 838 | 10/1996 |
| EP | 0 753 293 | 1/1997 |
| EP | 0 759 790 | 3/1997 |
| EP | 0 491 426 | 4/1997 |
| EP | 0 563 120 | 10/1997 |
| EP | 0 799 646 | 10/1997 |
| EP | 0 580 572 | 11/1997 |
| EP | 0 533 747 | 1/1998 |
| EP | 0 659 095 | 4/1998 |
| EP | 0 617 628 | 5/1998 |
| EP | 0 632 734 | 6/1998 |
| EP | 0 585 379 | 9/1998 |
| EP | 0 895 788 | 2/1999 |
| EP | 0 900 100 | 3/1999 |
| EP | 0 773 807 | 10/1999 |
| EP | 0 695 201 | 11/1999 |
| EP | 0 957 961 | 11/1999 |
| EP | 0 574 038 | 2/2000 |
| EP | 0 732 952 | 5/2000 |
| EP | 0 477 222 | 8/2000 |
| EP | 1 038 544 | 9/2000 |
| EP | 1 044 692 | 10/2000 |
| EP | 1 080 743 | 3/2001 |
| EP | 1 067 980 | 7/2001 |
| EP | 1 119 826 | 8/2001 |
| EP | 0 835 148 | 9/2001 |
| EP | 0 634 184 | 10/2001 |
| EP | 0 836 496 | 10/2001 |
| EP | 0 837 710 | 11/2001 |
| EP | 0 640 354 | 12/2001 |
| EP | 0 938 907 | 12/2001 |
| EP | 1 163 921 | 12/2001 |
| EP | 0 746 366 | 1/2002 |
| EP | 0 668 787 | 2/2002 |
| EP | 1 177 805 | 2/2002 |
| EP | 0 865 301 | 5/2002 |
| EP | 0 902 701 | 8/2002 |
| EP | 0 705 614 | 9/2002 |
| EP | 0 977 605 | 9/2002 |
| EP | 1 239 905 | 9/2002 |
| EP | 1 258 264 | 11/2002 |
| EP | 0 979 661 | 12/2002 |
| EP | 0 971 764 | 2/2003 |
| EP | 0 973 570 | 2/2003 |
| EP | 0 796 628 | 5/2003 |
| EP | 0 830 164 | 6/2003 |
| EP | 1 073 594 | 7/2003 |
| EP | 1 042 027 | 12/2003 |
| EP | 1 115 440 | 3/2004 |
| EP | 1 407 794 | 4/2004 |
| EP | 1 115 441 | 7/2004 |
| EP | 1 154 815 | 7/2004 |

(56) References Cited

FOREIGN PATENT DOCUMENTS

| | | |
|---|---|---|
| EP | 0 917 476 | 9/2004 |
| EP | 0 957 960 | 9/2004 |
| EP | 1 115 442 | 9/2004 |
| EP | 1 100 572 | 10/2004 |
| EP | 1 042 024 | 11/2004 |
| EP | 1 115 443 | 3/2005 |
| EP | 1 166 812 | 8/2005 |
| EP | 0 843 564 | 9/2005 |
| EP | 1 569 710 | 9/2005 |
| EP | 1 272 243 | 10/2005 |
| EP | 1 019 125 | 11/2005 |
| EP | 1 320 399 | 11/2005 |
| EP | 1 590 027 | 11/2005 |
| EP | 1 237 604 | 12/2005 |
| EP | 1 137 453 | 2/2006 |
| EP | 1 142 601 | 2/2006 |
| EP | 1 224 003 | 3/2006 |
| EP | 1 632 260 | 3/2006 |
| EP | 1 056 496 | 4/2006 |
| EP | 1 245 243 | 5/2006 |
| EP | 1 673 124 | 6/2006 |
| EP | 1 037 683 | 7/2006 |
| EP | 1 152 786 | 8/2006 |
| EP | 1 244 487 | 10/2006 |
| EP | 1 229 953 | 11/2006 |
| EP | 1 296 733 | 11/2006 |
| EP | 1 741 460 | 1/2007 |
| EP | 1 322 360 | 2/2007 |
| EP | 1 762 264 | 3/2007 |
| EP | 1 769 817 | 4/2007 |
| EP | 1 769 818 | 4/2007 |
| EP | 1 522 325 | 6/2007 |
| EP | 1 857 132 | 11/2007 |
| EP | 1 875 936 | 1/2008 |
| EP | 1 267 977 | 7/2008 |
| EP | 1 392 382 | 8/2008 |
| EP | 1 964 564 | 9/2008 |
| EP | 1 992 374 | 11/2008 |
| EP | 1 992 375 | 11/2008 |
| EP | 1 992 381 | 11/2008 |
| EP | 1 061 982 | 12/2008 |
| EP | 1 257 311 | 12/2008 |
| EP | 1 390 091 | 1/2009 |
| EP | 1 611 958 | 1/2009 |
| EP | 2 011 534 | 1/2009 |
| EP | 2 022 526 | 2/2009 |
| EP | 2 022 527 | 2/2009 |
| EP | 1 576 978 | 3/2009 |
| EP | 2 030 645 | 3/2009 |
| EP | 1 318 849 | 4/2009 |
| EP | 2 263 652 | 2/2010 |
| EP | 1 446 172 | 4/2010 |
| EP | 2 014 325 | 4/2010 |
| EP | 1 069 887 | 7/2010 |
| EP | 1 397 174 | 8/2010 |
| EP | 1 707 232 | 8/2010 |
| EP | 2 239 003 | 10/2010 |
| EP | 2 260 717 | 12/2010 |
| GB | 2046575 A * | 11/1980 ................ A24F 7/02 |
| GB | 2 224 446 | 5/1990 |
| GB | 2 230 456 | 10/1990 |
| GB | 2 263 068 | 7/1993 |
| GB | 2 263 873 | 8/1993 |
| GB | 2 299 512 | 10/1996 |
| GB | 2 340 758 | 3/2000 |
| GB | 2 344 533 | 6/2000 |
| GB | 2 354 451 | 3/2001 |
| GB | 2 426 202 | 11/2006 |
| GB | 2 446 781 | 8/2008 |
| GB | 2 447 606 | 9/2008 |
| JP | 6-501176 | 2/1994 |
| JP | 2003-514660 | 4/2003 |
| JP | 2004-290491 | 10/2004 |
| JP | 3-619176 | 2/2005 |
| JP | 2005-111328 | 4/2005 |
| JP | 3685671 | 8/2005 |
| JP | 2005-342353 | 12/2005 |
| JP | 3739955 | 1/2006 |
| JP | 3742517 | 2/2006 |
| JP | 3747076 | 2/2006 |
| JP | 2006-142119 | 6/2006 |
| JP | 3794710 | 7/2006 |
| JP | 3811827 | 8/2006 |
| JP | 2006-255308 | 9/2006 |
| JP | 2006-305281 | 11/2006 |
| JP | 2006-312086 | 11/2006 |
| JP | 3845530 | 11/2006 |
| JP | 3-960916 | 8/2007 |
| JP | 2008-012520 | 1/2008 |
| JP | 2008-036459 | 2/2008 |
| JP | 2008-049339 | 3/2008 |
| JP | 2008-183480 | 8/2008 |
| JP | 2008-264778 | 11/2008 |
| JP | 4189034 | 12/2008 |
| JP | 4195005 | 12/2008 |
| JP | 2009-045441 | 3/2009 |
| JP | 2009-183707 | 8/2009 |
| JP | 2009-254845 | 11/2009 |
| JP | 2009-261913 | 11/2009 |
| JP | 2010-057950 | 3/2010 |
| JP | 4469972 | 6/2010 |
| JP | 4572075 | 10/2010 |
| JP | 4580933 | 11/2010 |
| JP | 2010-279733 | 12/2010 |
| JP | 4589862 | 12/2010 |
| KR | 10-0805992 | 2/2008 |
| KR | 10-2009-0037906 | 4/2009 |
| KR | 10-2010-0134565 | 12/2010 |
| WO | WO 90/07351 | 7/1990 |
| WO | WO 90/13335 | 11/1990 |
| WO | WO 92/05825 | 4/1992 |
| WO | WO 92/07599 | 5/1992 |
| WO | WO 92/07600 | 5/1992 |
| WO | WO 92/12749 | 8/1992 |
| WO | WO 92/17231 | 10/1992 |
| WO | WO 94/04210 | 3/1994 |
| WO | WO 94/05358 | 3/1994 |
| WO | WO 94/05359 | 3/1994 |
| WO | WO 94/09842 | 5/1994 |
| WO | WO 94/19042 | 9/1994 |
| WO | WO 95/11715 | 5/1995 |
| WO | WO 95/17917 | 7/1995 |
| WO | WO 95/22365 | 8/1995 |
| WO | WO 95/26769 | 10/1995 |
| WO | WO 96/12470 | 5/1996 |
| WO | WO 96/32978 | 10/1996 |
| WO | WO 98/07464 | 2/1998 |
| WO | WO 98/41265 | 9/1998 |
| WO | WO 98/46280 | 10/1998 |
| WO | WO 98/51359 | 11/1998 |
| WO | WO 98/58695 | 12/1998 |
| WO | WO 99/12596 | 3/1999 |
| WO | WO 99/12597 | 3/1999 |
| WO | WO 99/26689 | 6/1999 |
| WO | WO 99/30760 | 6/1999 |
| WO | WO 99/36116 | 7/1999 |
| WO | WO 99/53982 | 10/1999 |
| WO | WO 99/65550 | 12/1999 |
| WO | WO 00/01435 | 1/2000 |
| WO | WO 01/26720 | 4/2001 |
| WO | WO 01/34232 | 5/2001 |
| WO | WO 01/38002 | 5/2001 |
| WO | WO 01/51112 | 7/2001 |
| WO | WO 01/78817 | 10/2001 |
| WO | WO 01/87378 | 11/2001 |
| WO | WO 01/97887 | 12/2001 |
| WO | WO 02/00279 | 1/2002 |
| WO | WO 02/05881 | 1/2002 |
| WO | WO 02/11801 | 2/2002 |
| WO | WO 02/11894 | 2/2002 |
| WO | WO 02/30501 | 4/2002 |
| WO | WO 02/43794 | 6/2002 |
| WO | WO 02/56948 | 7/2002 |
| WO | WO 02/81016 | 10/2002 |

(56) References Cited

FOREIGN PATENT DOCUMENTS

| | | |
|---|---|---|
| WO | WO 02/89875 | 11/2002 |
| WO | WO 02/89883 | 11/2002 |
| WO | WO 02/92146 | 11/2002 |
| WO | WO 02/10470 | 12/2002 |
| WO | WO 03/068254 | 8/2003 |
| WO | WO 03/088945 | 10/2003 |
| WO | WO 2004/022243 | 3/2004 |
| WO | WO 2004/101790 | 11/2004 |
| WO | WO 2005/060366 | 7/2005 |
| WO | WO 2005/074924 | 8/2005 |
| WO | WO 2005/080427 | 9/2005 |
| WO | WO 2005/087299 | 9/2005 |
| WO | WO 2007/117675 | 10/2005 |
| WO | WO 2005/120614 | 12/2005 |
| WO | WO 2006/022715 | 3/2006 |
| WO | WO 2006/031712 | 3/2006 |
| WO | WO 2006/133941 | 12/2006 |
| WO | WO 2007/073302 | 6/2007 |
| WO | WO 2007/106686 | 9/2007 |
| WO | WO 2007/107796 | 9/2007 |
| WO | 2007/117675 | 10/2007 |
| WO | WO 2007/117675 | 10/2007 |
| WO | WO 2007/118490 | 10/2007 |
| WO | WO 2007/136439 | 11/2007 |
| WO | WO 2008/023017 | 2/2008 |
| WO | WO 2008/024728 | 2/2008 |
| WO | WO 2008/028092 | 3/2008 |
| WO | WO 2008/029216 | 3/2008 |
| WO | WO 2008/053192 | 5/2008 |
| WO | WO 2008/060558 | 5/2008 |
| WO | WO 2008/087418 | 7/2008 |
| WO | WO 2008/110809 | 9/2008 |
| WO | WO 2008/117322 | 10/2008 |
| WO | WO 2008/139490 | 11/2008 |
| WO | WO 2008/140371 | 11/2008 |
| WO | WO 2009/003989 | 1/2009 |
| WO | WO 2009/004465 | 1/2009 |
| WO | WO 2009/007352 | 1/2009 |
| WO | WO 2009/007687 | 1/2009 |
| WO | WO 2009/009013 | 1/2009 |
| WO | WO 2009/009775 | 1/2009 |
| WO | WO 2009/015286 | 1/2009 |
| WO | WO 2009/016655 | 2/2009 |
| WO | WO 2009/022139 | 2/2009 |
| WO | WO 2009/022347 | 2/2009 |
| WO | WO 2009/029027 | 3/2009 |
| WO | WO 2009/029028 | 3/2009 |
| WO | WO 2009/029029 | 3/2009 |
| WO | WO 2009/061895 | 5/2009 |
| WO | WO 2009/075794 | 6/2009 |
| WO | WO 2009/083244 | 7/2009 |
| WO | WO 2009/087407 | 7/2009 |
| WO | WO 2009/090083 | 7/2009 |
| WO | WO 2009/091780 | 7/2009 |
| WO | WO 2009/092434 | 7/2009 |
| WO | WO 2009/092520 | 7/2009 |
| WO | WO 2009/092550 | 7/2009 |
| WO | WO 2009/092551 | 7/2009 |
| WO | WO 2009/092591 | 7/2009 |
| WO | WO 2009/092592 | 7/2009 |
| WO | WO 2009/092594 | 7/2009 |
| WO | WO 2009/092650 | 7/2009 |
| WO | WO 2009/100383 | 8/2009 |
| WO | WO 2009/112539 | 9/2009 |
| WO | WO 2009/117112 | 9/2009 |
| WO | WO 2009/121020 | 10/2009 |
| WO | WO 2009/132791 | 11/2009 |
| WO | WO 2009/133555 | 11/2009 |
| WO | WO 2009/139731 | 11/2009 |
| WO | WO 2009/139732 | 11/2009 |
| WO | WO 2009/139733 | 11/2009 |
| WO | WO 2009/140587 | 11/2009 |
| WO | WO 2009/151408 | 12/2009 |
| WO | WO 2009/158300 | 12/2009 |
| WO | WO 2010/007361 | 1/2010 |
| WO | WO 2010/008424 | 1/2010 |
| WO | WO 2010/039200 | 4/2010 |
| WO | WO 2010/040779 | 4/2010 |
| WO | WO 2010/070329 | 6/2010 |
| WO | WO 2010/070330 | 6/2010 |
| WO | WO 2010/073148 | 7/2010 |
| WO | WO 2010/075240 | 7/2010 |
| WO | WO 2010/094305 | 8/2010 |
| WO | WO 2010/097119 | 9/2010 |
| WO | WO 2010/116175 | 10/2010 |
| WO | WO 2010/129753 | 11/2010 |
| WO | WO 2010/133321 | 11/2010 |
| WO | WO 2010/133322 | 11/2010 |
| WO | WO 2010/133323 | 11/2010 |
| WO | WO 2010/135253 | 11/2010 |
| WO | WO 2010/135340 | 11/2010 |
| WO | WO 2010/136134 | 12/2010 |
| WO | WO 2010/142418 | 12/2010 |
| WO | WO 2010/145894 | 12/2010 |
| WO | WO 2010/149280 | 12/2010 |
| WO | WO 2010/149345 | 12/2010 |

OTHER PUBLICATIONS

Lostetter, Yorick, "European Search Report", EP Application No. EP12183731, issued on Oct. 17, 2012 (5 pages).
Lostetter, Yorick, "European Search Report", EP Application No. EP12183733, issued on Oct. 17, 2012 (5 pages).
English Version of Office Action dated Oct. 29, 2013 from Corresponding Japanese Patent Application No. 2010-538005.
European Office Action dated Mar. 30, 2015 from corresponding European Application No. 12183733.0.
Japan Patent Office, "Notice of Reasons for Rejection (Translated)", Japan Application No. 2010-538005, mailed on Jan. 22, 2013 (2 pages).

* cited by examiner

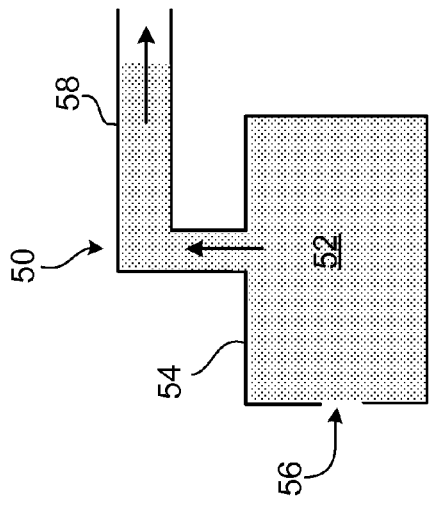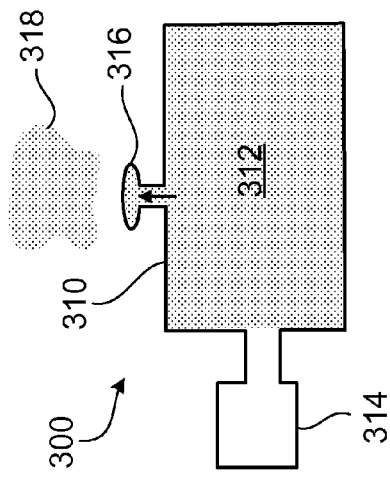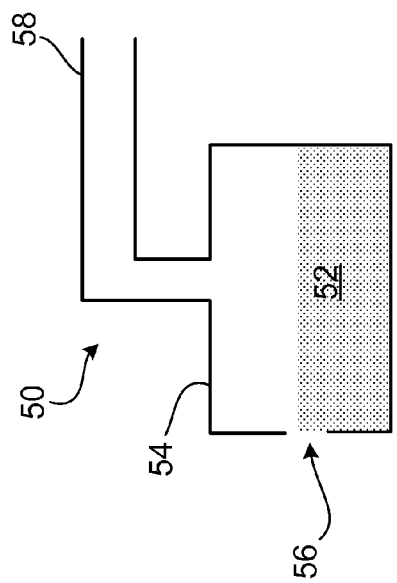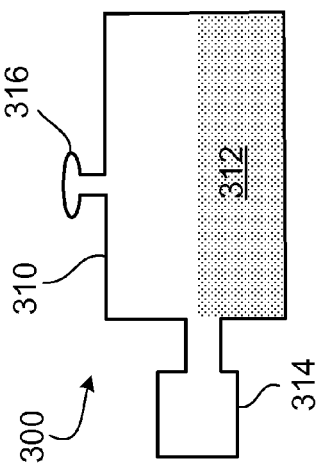

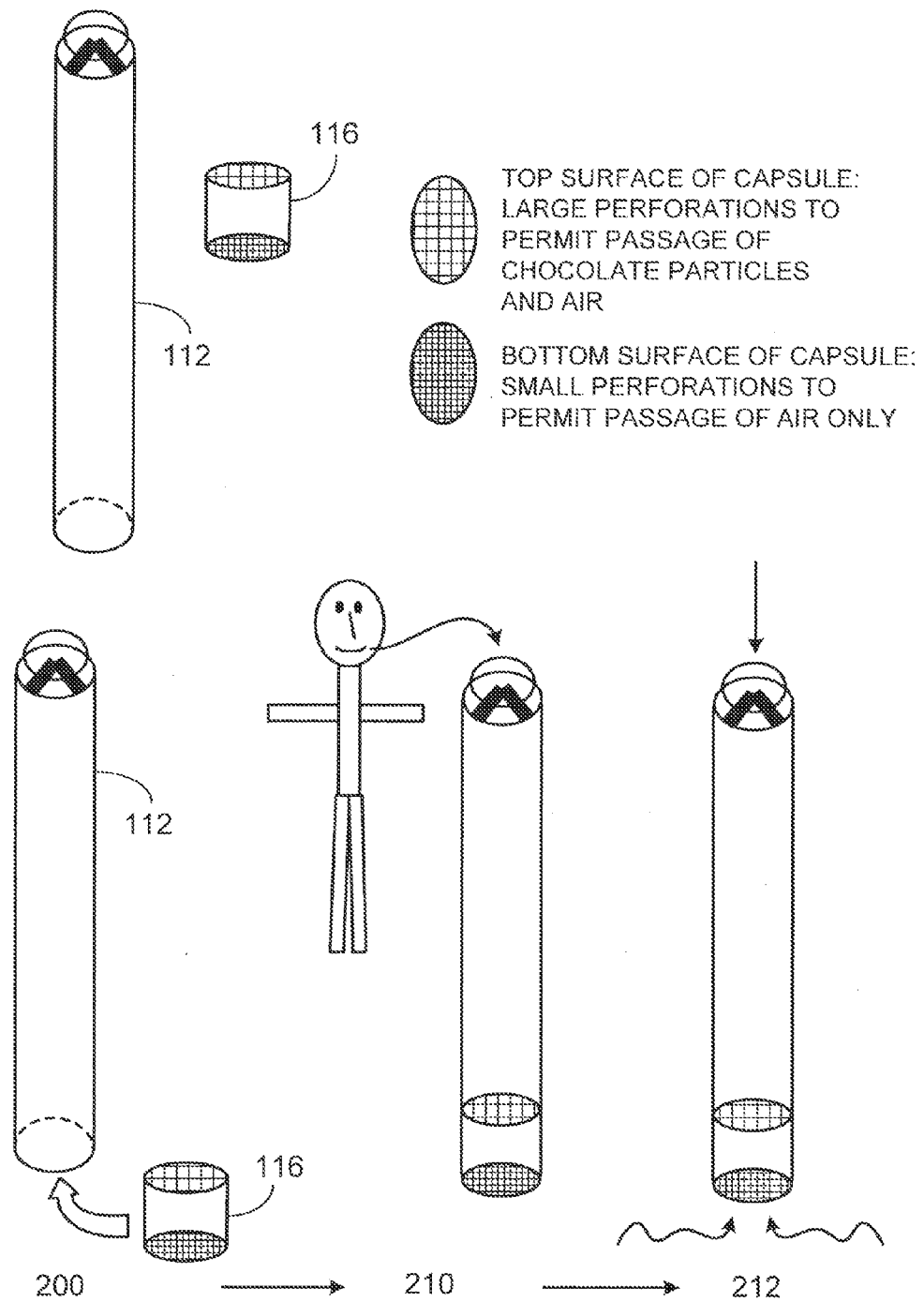

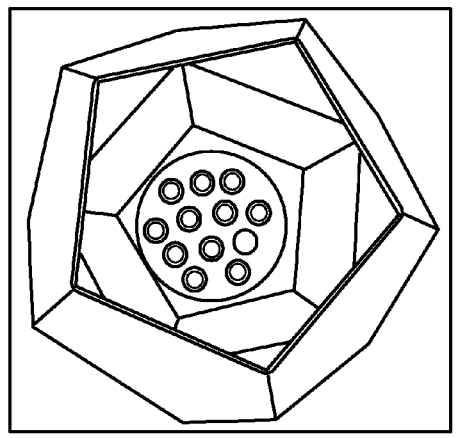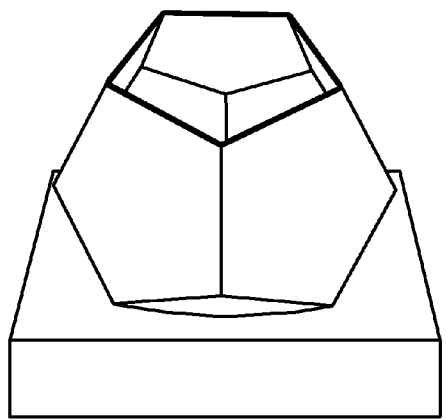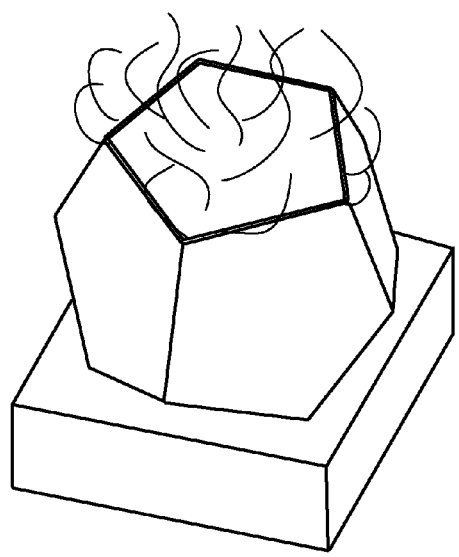
FIG. 13

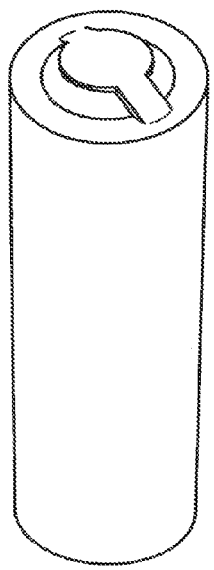
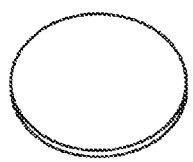
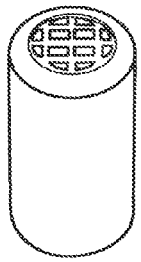
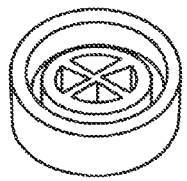
HOUSING  CAPSULE  CAP
FIG. 16A  FIG. 16B  FIG. 16C

TOP VIEW (HOUSING, CAPSULE, CAP)

TOP AND BOTTOM VIEWS OF CAPSULE(GRATING ON TOP;
OPEN ON BOTTOM>

HOUSING + CAPSULE + CAP

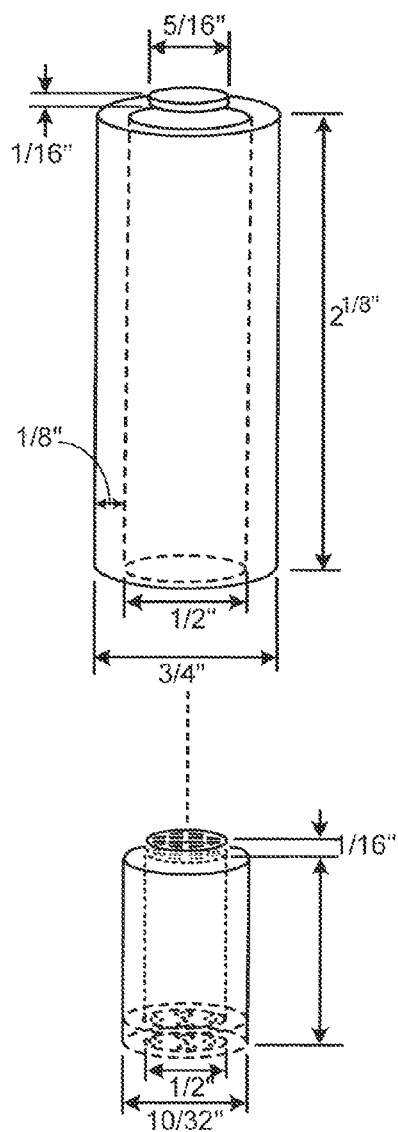
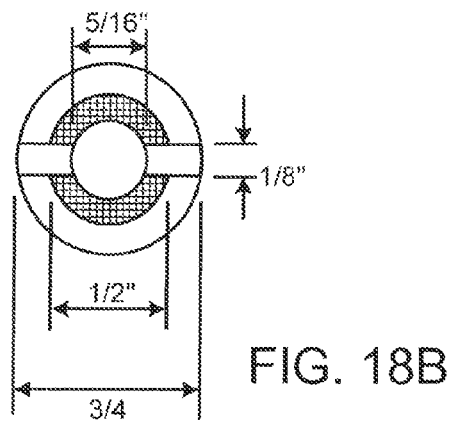
FIG. 18B
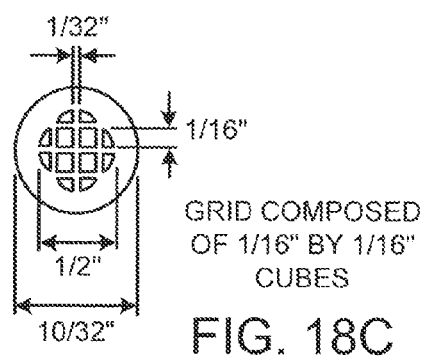
GRID COMPOSED OF 1/16" BY 1/16" CUBES
FIG. 18C
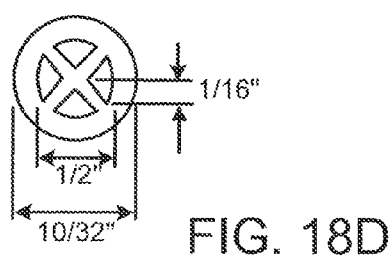
FIG. 18D
FIG. 18A

DELIVERING AEROSOLIZABLE FOOD PRODUCTS

This application is the National Stage of International Application No. PCT/US2008/079214, filed on Oct. 8, 2008, which claims priority to U.S. Provisional Application Ser. No. 61/013,861, filed on Dec. 14, 2007, and U.S. Provisional Application Ser. No. 61/039,783, filed on Mar. 26, 2008. The contents of the above-referenced applications are hereby incorporated by reference in their entireties.

FIELD OF THE INVENTION

The invention relates generally to aerosolized food products and apparatus for the containment, aerosolization, and/or delivery thereof.

BACKGROUND OF THE INVENTION

Previous researchers have demonstrated that aerosol particles can be used to deliver substances to various parts of the body. Certain designs have been proposed for utilizing these particles for drug delivery.

SUMMARY OF THE INVENTION

When inhaling particles that are sufficiently light to enter the mouth, one must address the risk of those particles reaching the back of the mouth or lungs and causing coughing or other adverse events.

Therefore, approaches to deliver materials to the mouth via the airborne route have largely (if not exclusively) focused on directed, non-breath-actuated delivery, where the force of the air current and size of the particles are such that particle trajectories are primarily limited to within the mouth.

We have developed an approach by which a casual or forced breathing maneuver (such as normal inhalation) can lead to the delivery of food (or various other) particles to the mouth, in which the transport of these particles with the flowing air, to the back of the throat and to the lungs, is limited. By controlling the inertia and gravity of the food particles, and be directing deposition forces, we can focus the delivery towards surfaces of the mouth, not reaching the back of the throat and lungs.

There are 2 practical aspects to our approach:
 1. Particle size is extremely important to our delivery system, namely that the particles need to be small enough to remain airborne during casual breathing, but large enough to be directed and deposited primarily in the mouth while limiting throat and lung deposition.
 2. At the same time, typical pathways of aerosol particles through the device and out of the mouthpiece are directed to varying degrees away from the back of the throat.

The combination of appropriate particle size and device-directed air pathway leads to the food particles depositing primarily in the mouth (and onto the tongue, palate, etc.) rather than at the back of the throat or further into the respiratory tract.

In one aspect, the approach is directed to aerosolized food particles of sufficient size to primarily deposit in the mouth with limited entry into the respiratory tract and of small enough size so as to allow for suspension in air. In another aspect, the approach is directed to an apparatus incorporating food products, an aerosol generating device to allow for the aerosolization of the food products, and a delivery device that delivers the aerosolized food products in a manner suitable for inhalation or deposition and subsequent ingestion. In another aspect, the approach is directed to airflow-directing elements in an apparatus or device for the delivery of food products by aerosol. These elements, by controlling the gravity, inertia, and other forces relevant to the aerosol cloud upon delivery of the cloud to the mouth, substantially divert the aerosol cloud to surfaces in the mouth and decrease the extent to which the cloud can continue to the throat and further into the respiratory tract.

Our apparatus represents a novel means of delivering food to the mouths of humans and animals. Indeed, the apparatus is designed to produce aerosolized food particles of sufficient size to deposit in the mouth without substantial exposure or entry into the respiratory tract and of small enough size so as to allow for suspension in air.

In some embodiments, our apparatus generates an aerosol cloud of food particles that enters the mouth of humans or animals by inhalation, bodily movement, and/or aerosol movement, or a combination thereof, in a manner distinct from conventional means of mechanical delivery, i.e., the use of utensils, and conventional means of mechanical digestion of food, i.e., by chewing or sucking. For example, simple inhalation may serve to allow the food particles to deposit within the digestive tract including the mouth of a subject.

Alternatively or in combination, a subject may physically expose himself or herself to the food particles released from the apparatus by a simple bodily movement, such as walking or leaning such that the subject's mouth is exposed to the food particles thereby leading to food deposition in the mouth. Alternatively or in combination, a subject may physically expose himself or herself to the food particles released from the apparatus by a simple aerosol movement, such as an air current carrying the aerosol, or a small container in which a user carries the aerosol, such that the subject's mouth is exposed to the food particles thereby leading to food deposition in the mouth.

Our apparatus generally includes food products and an aerosol generating device. In some embodiments, the apparatus includes food product, an aerosol generating device, and an air intake passage. In some embodiments, the apparatus includes a mouthpiece. In some embodiments, the apparatus consists solely of a mouthpiece. The apparatus may be activated by inhalation at the mouthpiece, thereby resulting in the exposure of the food product to the aerosol generating device and the subsequent aerosolization of the food product. The inhalation further serves to deliver the aerosolized food product to the mouth of the subject.

In some embodiments, the apparatus includes food product, an aerosol generating device, and a force generating device, for example, an air pump. The apparatus may be activated by way of the force generating device, thereby resulting in the exposure of the food product to the aerosol generating device, the subsequent aerosolization of the food product and the emission thereof from the device.

In some embodiments, the apparatus includes food product and an aerosol generating device, for example, an ultrasound source. The apparatus may be activated by way of the aerosol generating device, which may atomize and/or aerosolize the food product and emit the food product from the device.

In some embodiments, the apparatus may incorporate a delivery device.

BRIEF DESCRIPTION OF THE DRAWINGS

The advantages of the invention described below, as well as further advantages of the invention, can be better understood by reference to the description taken in conjunction with the accompanying figures, in which:

FIGS. 1A and 1B are schematics of an embodiment of a food delivery apparatus, respectively, before use and during use.

FIG. 3 is a schematic of a particular embodiment of the food delivery apparatus and a diagram for its use and operation.

FIGS. 7A and 7B are schematics of a food delivery apparatus, respectively, before use and during use.

FIG. 13 includes photographs of a food delivery apparatus at different stages of use.

FIGS. 16A-16C and 17A-17C are illustrations of a food delivery device. The food delivery devices include a housing, a mouthpiece formed therewith, an airflow directing element attached therewith via bridges, a capsule having air passageways and grating, and a cap having air passageways and capable of snapping together with both the capsule and the housing. In some embodiments, the grating, here part of the capsule, serves as an aerosol-generating device.

FIGS. 18A-18D set forth the specifications of a particular embodiment of a food delivery apparatus. The food delivery apparatus includes a housing, a mouthpiece formed therewith, an airflow directing element attached therewith via bridges, a capsule having air passageways and grating, and a cap having air passageways and capable of snapping together with both the capsule and the housing.

DETAILED DESCRIPTION OF THE INVENTION

Figure 2A:
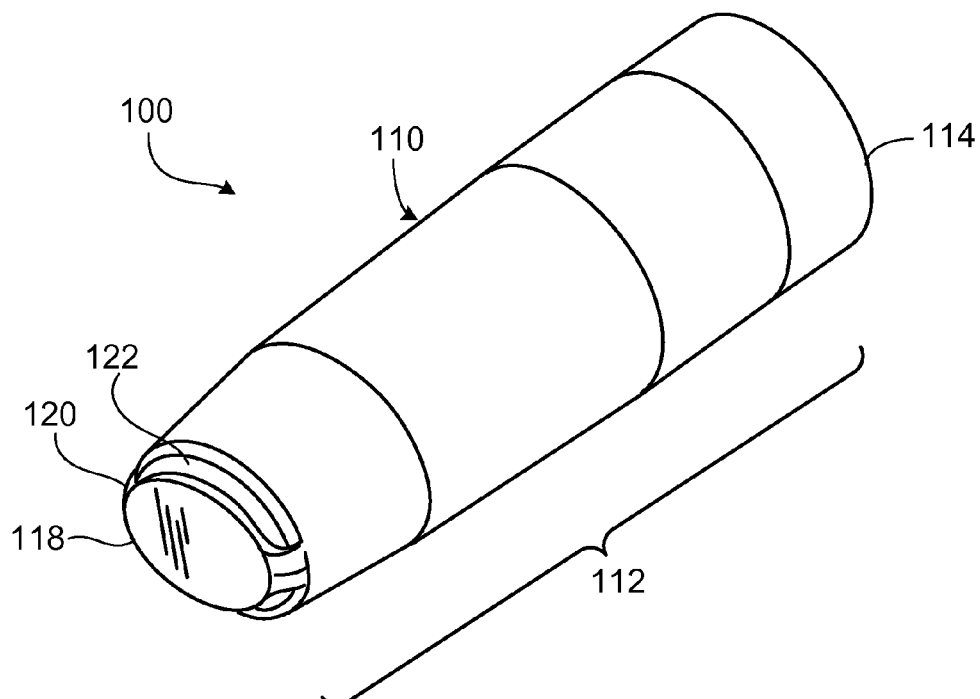
FIGS. 2A and 2B are perspective views of a food delivery device.
Figure 2B:
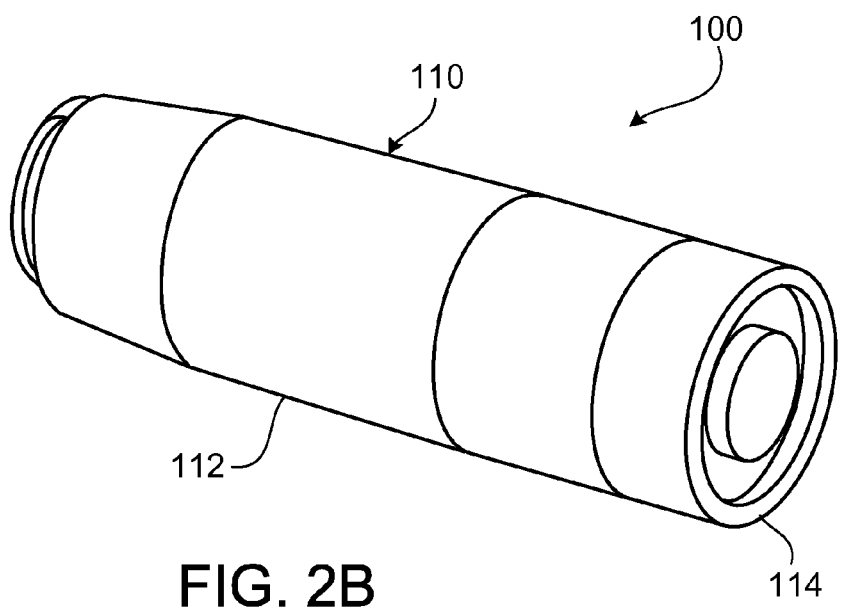
Figure 2C:
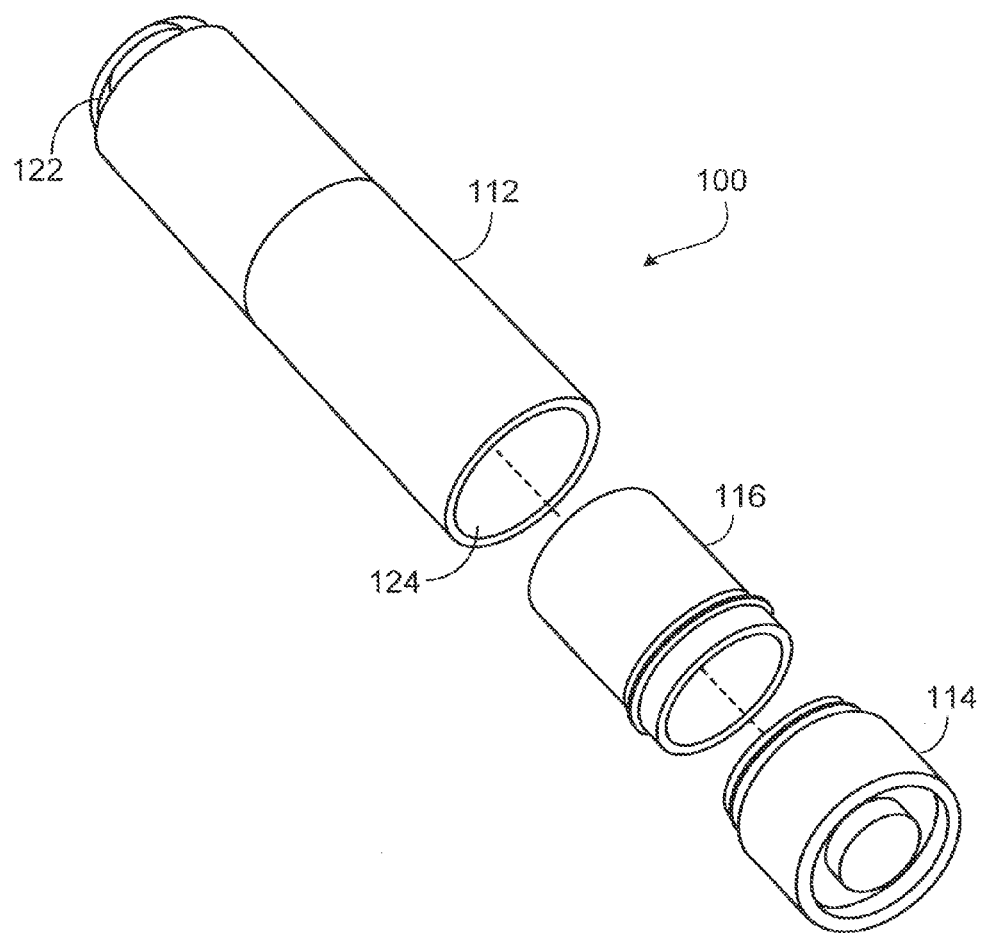
FIGS. 2C and 2D are, respectively, an exploded perspective view and a cut-away perspective view of the food delivery device of FIGS. 2A and 2B.

Our approach is based, at least in part, on the realization of a new form of food and methods and apparatus for the delivery thereof. More specifically, the delivery technology and approach is directed to aerosolized food products and a food delivery method and apparatus designed to generate and deliver such products to a subject. Such devices can deliver food substances into the mouth by aerosol wherein the aerosol cloud is generated and delivered to the mouth through a natural inspiration maneuver and wherein the design of the mouthpiece of the device is such that the airborne food particles are diverted away from the back of the throat to limit entry into the respiratory system.

Referring to FIGS. 1A and 1B, a food delivery apparatus 50 includes an aerosol generating device, in which inhalation triggers the aerosolization of a food product 52 and subsequent delivery of the aerosolized food product to the mouth of a subject. The food delivery apparatus 50 includes a compartment 54 containing the food product 52 (e.g., a powdered food). The compartment 54 has an air intake passage 56 and is connected to a mouthpiece 58. The air intake passage 56, the compartment 54, and the mouthpiece 58 allow for the passage of air such that airflow generated by inhalation aerosolizes the food product 52 and transports the aerosolized food product out of the compartment 54, through the mouthpiece 58 and into the consumer's mouth.

Referring to FIGS. 2A-2F, a food delivery device 100 includes a housing 110 with a mouthpiece 112 and a detachable end cap 114. The food delivery device 100 is sized such that a user can easily hold the device in one hand while using the device 100 to generate and deliver an aerosolized food product. An airflow directing or deflection member 118 is disposed at one end of the mouthpiece 112 with bridges 120. The bridges 120 position the airflow directing member 118 in a location spaced apart from a plane of an outlet 122 of the mouthpiece 112. The end cap 114 is attached to the end of the mouthpiece 112 opposite the airflow directing member 118.

Figure 2D:
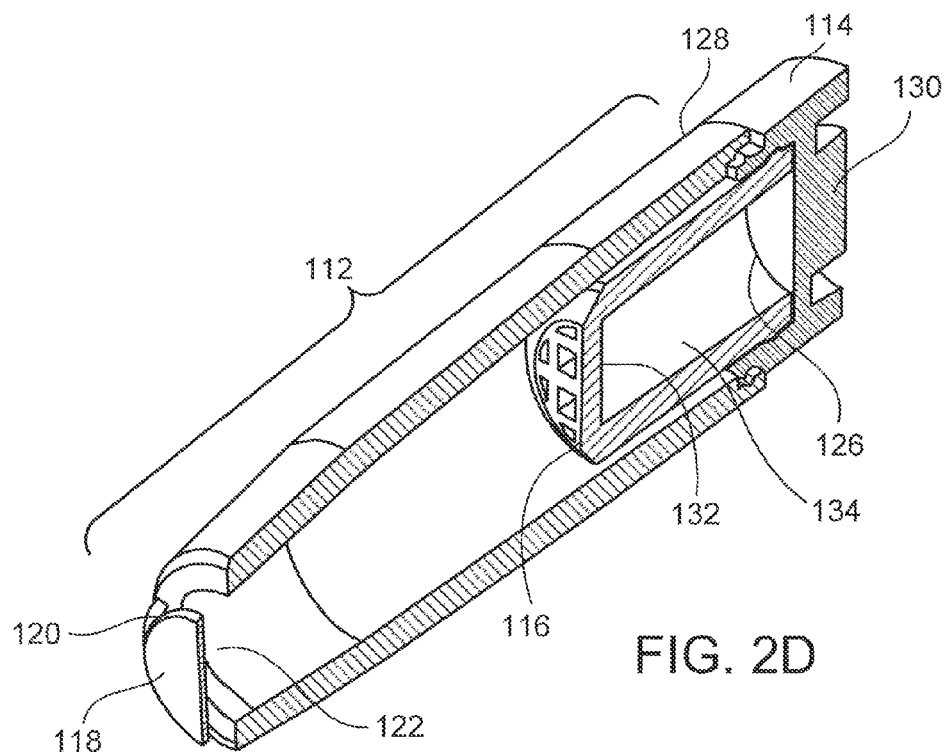
Figure 2E:
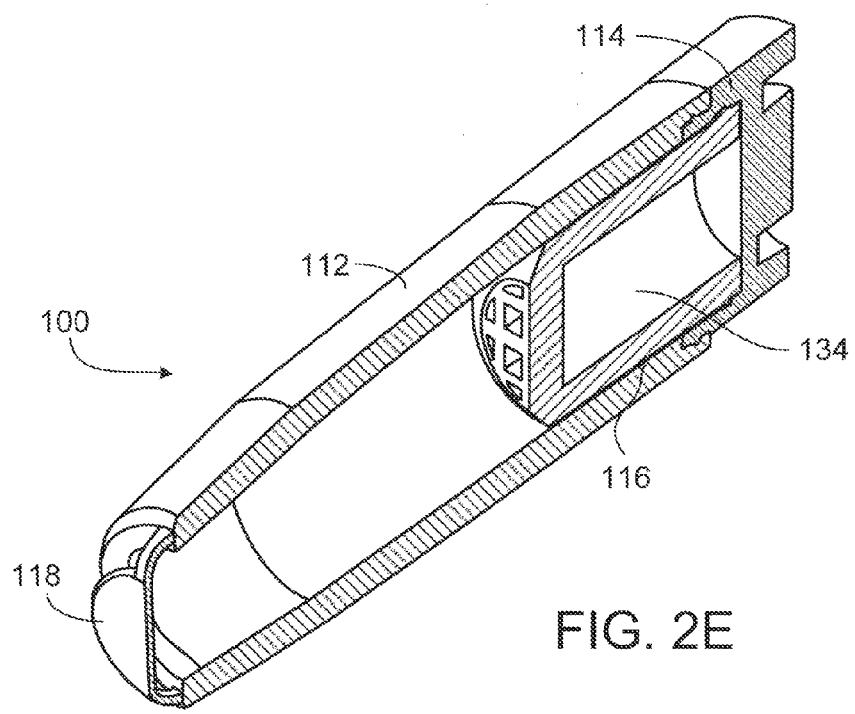
FIG. 2E is a cut-away perspective view of the food delivery device of FIGS. 2A and 2B FIGS. 2F and 2G, respectively are a cross-sectional views of the food delivery device of FIGS. 2A and 2B and of a portion of the food delivery device of FIGS. 2A and 2B.

As can be seen in FIG. 2D, the mouthpiece 112 defines a fluid flow passage extending from an inlet 124 to the outlet 122 of the mouthpiece 112. The end cap 114 has air passageways 126 extending from one face of the end cap 114 to an opposite face of the end cap 114. When the end cap 114 is attached to the mouthpiece 112 on the inlet end of the mouthpiece 112, the mouthpiece 112 and the end cap 114 together define a flow path through the housing 110. Thus, when a user places the outlet 122 of the mouthpiece 112 in his or her mouth and inhales, air flows through end cap 114, into the inlet 124 of the mouthpiece 112, and through the mouthpiece 112 to the outlet 122 of the mouthpiece 112. Contact with the airflow directing member 118 deflects the air flowing out of the mouthpiece 112.

In some embodiments, the airflow-directing element is a thin disc with a flat surface generally perpendicular to the axis of the mouthpiece and in opposition to the general airflow direction in the mouthpiece. In some cases, the disc may be mounted to the mouthpiece via one or more "bridges", which may, for example, hold the disc slightly above, below, or at the same level as the edge of the mouthpiece, allowing air, and the aerosolized food product to pass around the disc. In various embodiments, the disc may have a diameter smaller, equal to, or larger than the opening of the mouthpiece. Additionally, the disc may be of any desired shape, for example, an elliptical shape or round shape. The airflow-directing element redirects the aerosol to the sides of the mouth (e.g. top, bottom, left, right surfaces within the mouth), thereby limiting flow of the aerosol toward the throat where it might elicit a coughing reflex. Instead, the aerosolized food product deposits on the tongue or other parts of the mouth where it can be sensed and appreciated rather than carried deeper into the respiratory tract. In some embodiments, the airflow-directing element is of a different shape, size, and/or design but similarly serves to redirect the aerosolized food product so as to limit the coughing reflex and/or to enhance the taste experience. Testing of a variety of disc sizes and positions has shown that these two parameters can impact likelihood of coughing. For example, it was found in preliminary tests that a disc whose diameter is roughly equal to that of the external diameter of the mouthpiece, and that is placed close to the mouthpiece, is generally more effective in redirecting the aerosol and limiting coughing, than one whose diameter is roughly equal to that of the internal diameter of the mouthpiece (thus smaller) and that is placed at a greater distance from the mouthpiece (leaving a larger space for the aerosol to pass through).

In this embodiment, the end cap 114 is formed of a resilient material. A first end 128 of the end cap 114 has an outer surface that is sized and configured to provide a snap-fit engagement with the inner surface of the corresponding end of the mouthpiece 112. In some embodiments, other forms of engagement are used instead of or in addition to snap-fit engagement to attach the end cap 114 to the mouthpiece 112. For example, in some embodiments, the end cap 114 and the mouthpiece 112 have threads and are screwed together.

The mouthpiece 112 together with the end cap 114 (i.e., the housing) define an interior cavity sized to receive a capsule 116 such as, for example, a capsule 116 including a reservoir 134 containing a powdered food product (not shown). The capsule 116 is configured to provide fluid communication between the contents of the capsule 116, for example, a powdered food product, with the mouthpiece. In this embodiment, the capsule 116 has an open end 130 and an opposite aerosol generating end 132. The open end 130 of the capsule 116 fits within the first end 128 of the end cap 114 and is sized and configured to provide a snap-fit engagement with the inner surface of the first end 128 of the end cap 114. In some embodiments, the capsule may be snapped or screwed into the housing. In some embodiments, the capsule includes an open end that may be covered (in certain embodiments, only at certain times) by the cap, for example, by snapping or screwing. In some embodiments, the inlet end of the capsule defines air passages rather being open.

Figure 2F:
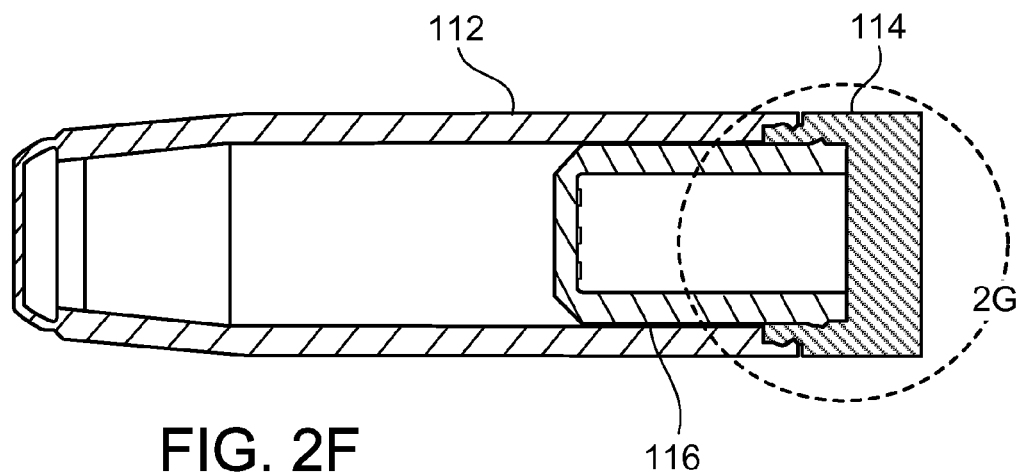
Figure 2G:
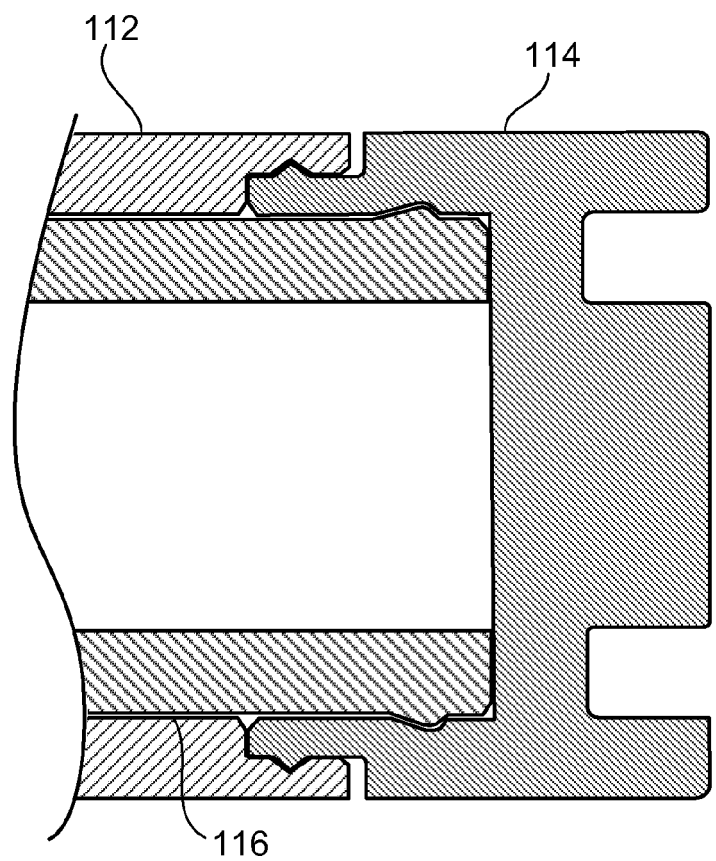

Referring to FIG. 2F, in some embodiments, the capsule 116 snaps into the cap 114 by a full annular snap mechanism on the inside of the cap 114, and the cap 114 snaps into the mouthpiece 112 by an interrupted snap mechanism. The device may thus be designed so that it is typically more difficult to separate the cap 114 from the capsule 116 than the cap 114 and/or capsule 116 from the mouthpiece 112. A user can then easily replace the capsule 116 and/or cap 114 by removing it from the mouthpiece 112, with minimal risk of accidentally detaching the capsule 116 from the cap 114.

Some embodiments may be further enhanced by incorporating snap mechanisms that facilitate the use and functionality of the device. For example, a device may incorporate snap mechanisms to facilitate the use of a mechanism like the one described above that allows for the opening and closing of air passageways. For example, the mouthpiece and capsule can be designed such that they are able to connect by one (or more) snap mechanism(s), and the capsule and cap able to connect by two (or more) snap mechanism(s). For example, the mouthpiece may be connected to the capsule by one relatively weak snap interface, and the capsule may be connected to the cap by two relatively strong snap interfaces. In some embodiments, these snap mechanisms can: (1) hold the capsule (or more generally, one end of the food-containing apparatus) to the mouthpiece (or more generally, to the delivery apparatus) ("snap A"); (2) hold the capsule and cap (or more generally, hold together the components of the food-containing apparatus) in an initial "closed" configuration that minimizes powder loss (especially relevant during shipping, handling, etc.), and may also serve to provide a protected, airtight or nearly airtight environment for the preservation of the food product before use ("snap B"); and (3) after user intervention, reconnect the capsule and cap (or more generally, the components of the food-containing apparatus) to maintain a new "open" configuration in which air can flow through the apparatus and enable subsequent aerosolization of the food product ("snap C").

The forces required to actuate each of these snaps plays a role in the functionality and ease of use of the device. They may be configured to allow use as follows: (1) the user attaches the capsule/cap component to the mouthpiece. Snap A is actuated. Now, the capsule is hidden within the mouthpiece and the cap. (2) The user now pulls back on the cap, undoing Snap B. With a strong Snap A, the capsule stays connected to the mouthpiece and the cap slides away from the mouthpiece. This relative motion between the capsule and cap allows for the air passageways to open, as described earlier. (3) The user continues to pull the cap back until Snap C is actuated, locking the capsule and cap in place in such a way as to leave the air passageways open. The user can now inhale and have the food product aerosolize and be delivered to the mouth. Once the food product is consumed, the high strength of this snap (C) allows the user to pull out the capsule/cap from the mouthpiece and replace it with a new capsule/cap, with minimal risk of separating the capsule from the cap instead (the capsule is simultaneously connected to the mouthpiece via snap A and connected to the cap by snap C; since snap C is engineered to be stronger than snap A, a force applied by the user that pulls the mouthpiece and cap in opposite directions generally leads to the capsule and cap detaching from the mouthpiece as one unit, thus undoing snap A). In some embodiments, snap C is also important in that it minimizes the user's ability to completely separate the capsule and cap, even after the mouthpiece is removed. In some cases, it may be desirable to prevent a user from attempting to add his/her own product, or otherwise tamper with the food product or food-containing compartment.

In many instances, variations of some embodiments may be designed without, in many instances, affecting the function of the overall device. For example, the cylindrical nature of the device may be modified, for example, for aesthetic effect, as may the overall length of the device. Alternatively, or in addition, the aerosol generating device, for example, the airflow disrupting element such as a grating, may be incorporated into the cylindrical mouthpiece unit. In some embodiments, the aerosol generating device may include more than one component. For example, a grating and/or the airflow passageways in the cap may play individual roles in generating turbulence that leads to aerosolization, or both may be needed. In general, there may also be multiple configurations of gratings, airflow passageways, dimensions etc., to produce the right aerosolization airflow.

In some embodiments, the dimensions of the device may be selected so that, while preserving the appropriate airflow dynamics, standard medical capsules may be used directly as the compartment, or may to some extent replace the previously described capsule and/or cap, or in another way simplify the process of loading, storing, and releasing the powder.

In some embodiments, the capsule and/or cap have concave inner spaces, and after powder is filled into either or both of them, the two units snap or screw together to form a largely closed interior chamber. The capsule, or another component of the device, should further include an aerosol generating device, for example, an airflow-disrupting "grating", through which air and powder flow, thereby yielding an aerosol for delivery to the user. The cap and/or the capsule should include air passageways, for example, on the respective ends of the enclosed compartments, so as to allow air to flow through upon inhalation. The design, for example, the size or shape of the air passageways, should provide sufficient airflow while minimizing powder loss.

In some embodiments, the cap 114 and/or the capsule 116 is designed to minimize powder loss. For example, as shown in FIG. 1E, the air passageways angle out to the sides, rather than straight through to the bottom, to limit powder from falling out due to gravity, even when the device is upright. When the powder is inside the capsule/cap, and shaking or other movements are minimal, powder may accumulate against the bottom surface of the passageways but minimally fall out through the side passageways.

In some embodiments, the need for balance between airflow and minimal powder loss can be achieved by a mechanism that enables air passageways to be alternatively open or closed. For example, in some embodiments, the capsule and cap components may fit together but remain capable of sliding against each other, to enable two configurations: in the closed configuration, the two are closer together, with elements at the base of the capsule blocking the air passageways of the cap; in the open configuration, the capsule and cap are separated slightly, allowing air to flow through the air passageways in the cap.

In some embodiments, the mouthpiece, capsule, and/or cap are designed for single use (perhaps disposable) or, alternatively, designed for multiple use. For example, in some embodiments, the capsule and cap may be disposable, and, optionally, available with a variety of food powders, while the mouthpiece may be reusable. In certain embodiments, pre-filled standard-sized capsules, for example, a gel capsule or blister pack, can be used. Such embodiments allow for easier filling, substitution, cleaning, and disposal. In addition, such embodiments allow for manufacture of multiple dose capsules. Such pre-filled capsules could be punctured, torn, cut or broken by design elements within the housing (for example, sharp points, blades, compressing the device, or twisting the device etc.) prior to use. The food product may thus be released into a chamber, for example, and become more susceptible to airflows generated during inhalation or activation; or the food product, as another example, may remain substantially within the original container but now be in fluidic communication with, and thus now susceptible to, airflows generated during inhalation and/or activation; etc. After activation and use, the emptied capsule could be removed from the compartment and disposed of conveniently. Alternatively, the capsule can be designed for multiple uses. For example, the capsule may be refillable.

In some embodiments, the housing is designed to allow for the incorporation of at least 2, for example, 3, 4, 5, 6, 7, 8, 9 or 10, capsules, thereby allowing, for example, the user to mix and match a variety of flavors in various amounts as desired. In some embodiments, the housing could be designed to allow for the loading of a set of multiple capsules to be activated one at a time, thus reducing the frequency of removing and replacing spent capsules.

In some embodiments, the device is designed for use by at least 2, for example, 3, 4, 5, 6, 7, 8, 9 or 10, users. For example, the device could be designed with multiple branches, each designed with an airflow directing element, so as to allow for simultaneous use by multiple users.

In certain aspects, the device includes a housing, a capsule and a cap. In alternative aspects, a device includes the housing and a cap, wherein both the housing and the cap are designed for use with capsules, for example, disposable or refillable capsules. In other aspects, the device encompasses disposable or refillable capsules. In other aspects, the device encompasses mouthpieces, used with a variety of aerosolized food products, aerosolized food product sources, and/or aerosolized food product containers.

It should be noted that the functionalities (i.e., food product containment, aerosol generation, aerosol delivery, airflow (and aerosol) direction, etc.) of the mouthpiece, capsule, cap, grating, mouthpiece disc, etc. may, in some embodiments, be associated with one or more potentially different physical units, while maintaining the same overall functionality. For example, in some embodiments, a single device unit may incorporate all functional aspects. In some embodiments, a mouthpiece may contain an aerosol generating device, an aerosol delivery device, and an airflow- (and aerosol-) directing device, and the food product container may be separate. In some embodiments, as previously described, food product may be contained within a capsule and cap, an aerosol generating device may be part of a capsule, and a mouthpiece with airflow-directing elements may be used to deliver the aerosol from the capsule/cap to the user.

Referring to FIG. 3, a user operates a food delivery device 100 by loading the device 100 (step 200); bringing the device 100 to the user's mouth (step 210); and inhaling through the mouthpiece 112 (step 212) thereby causing air to enter the cap and the capsule through the air passageways. The air compels the food powder present in the capsule 116 to aerosolize through the aerosol generating device, for example, the grating, and subsequently enter the user's mouth via the mouthpiece 112.

Figure 4:
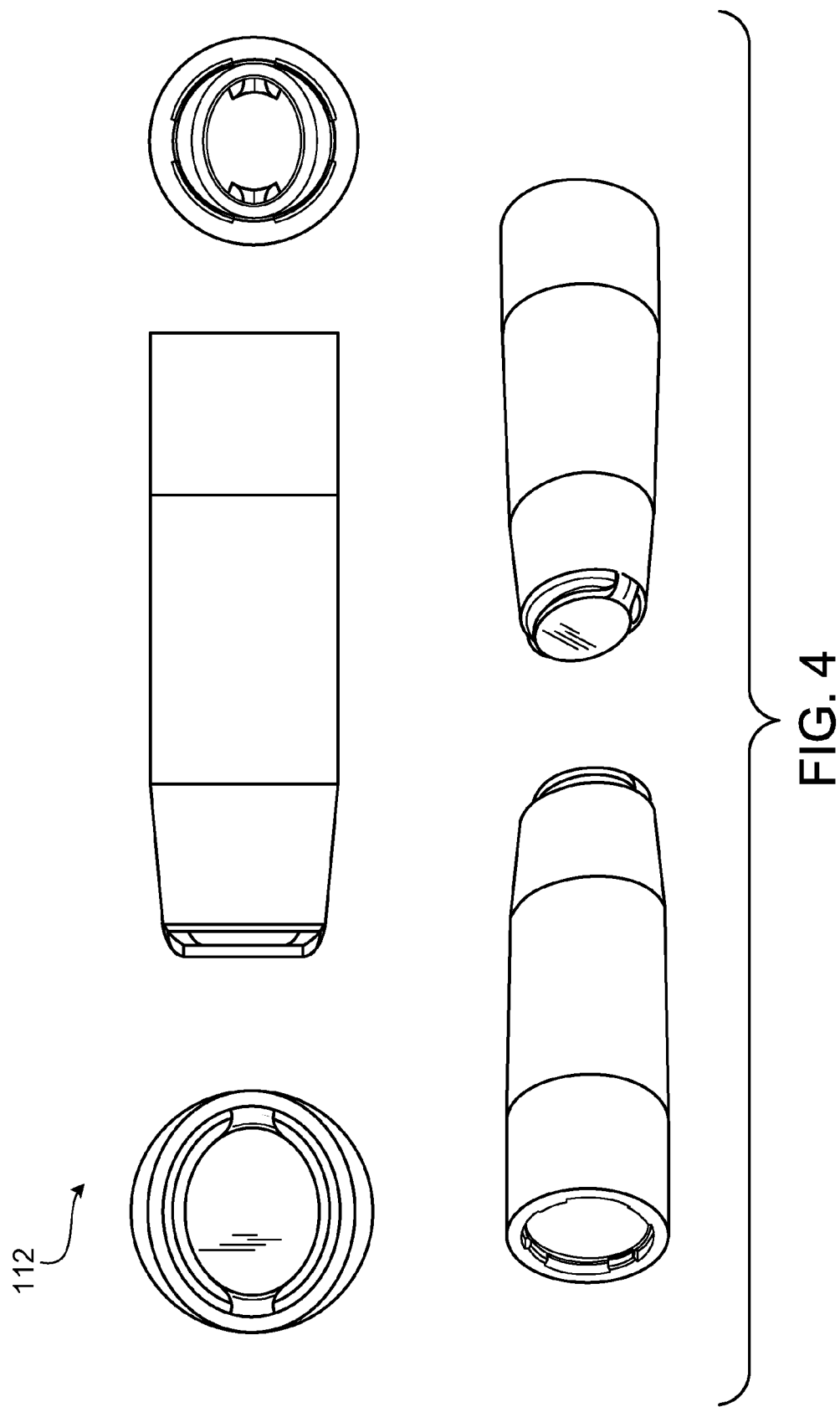
FIG. 4 presents multiple views of an exemplary embodiment of a mouthpiece 112.

FIG. 4 presents multiple views of an exemplary embodiment of a mouthpiece 112.

Figure 5:
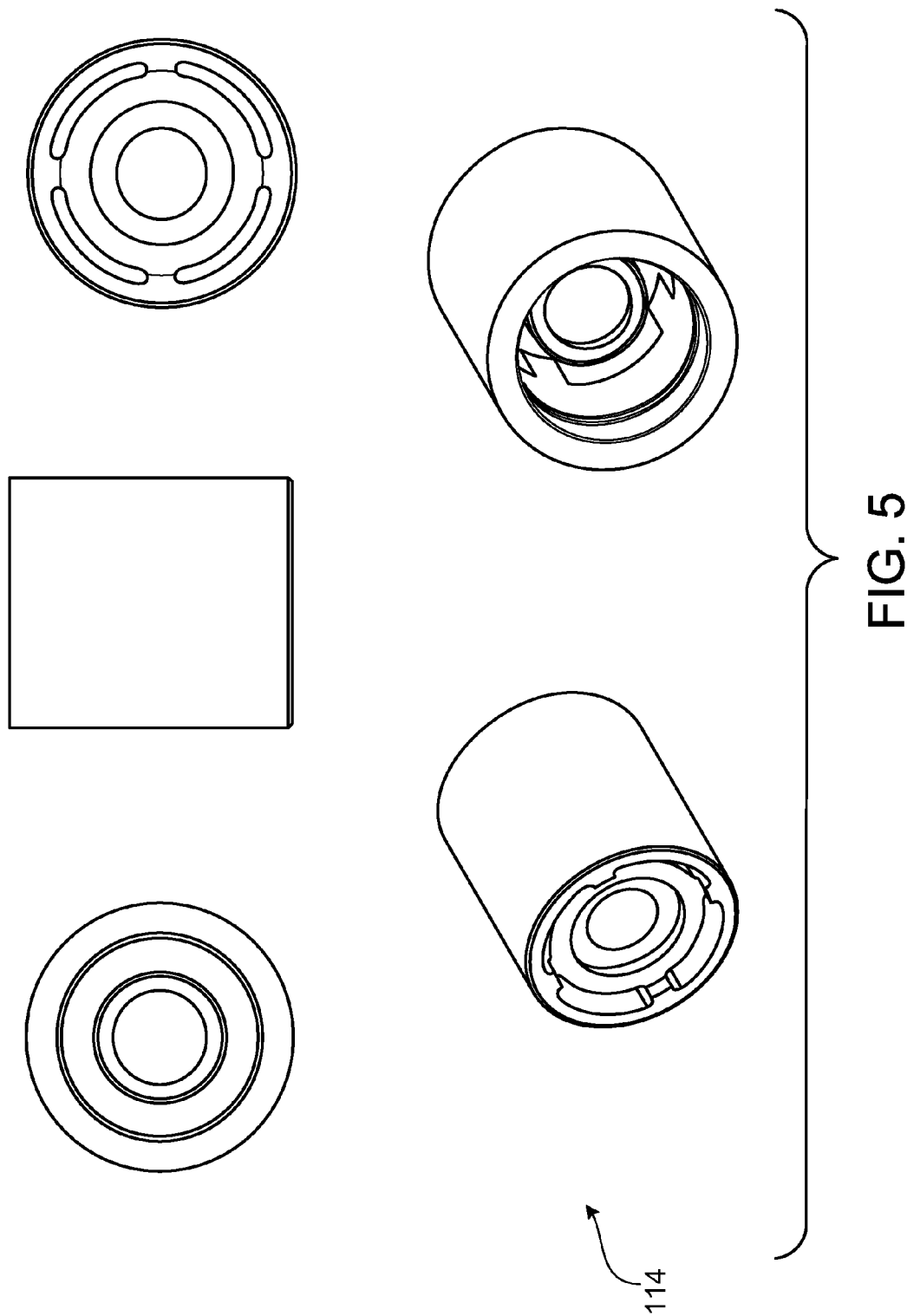
FIG. 5 presents multiple views of an exemplary embodiment of an end cap 114.

FIG. 5 presents multiple views of an exemplary embodiment of an end cap 114.

Figure 6:
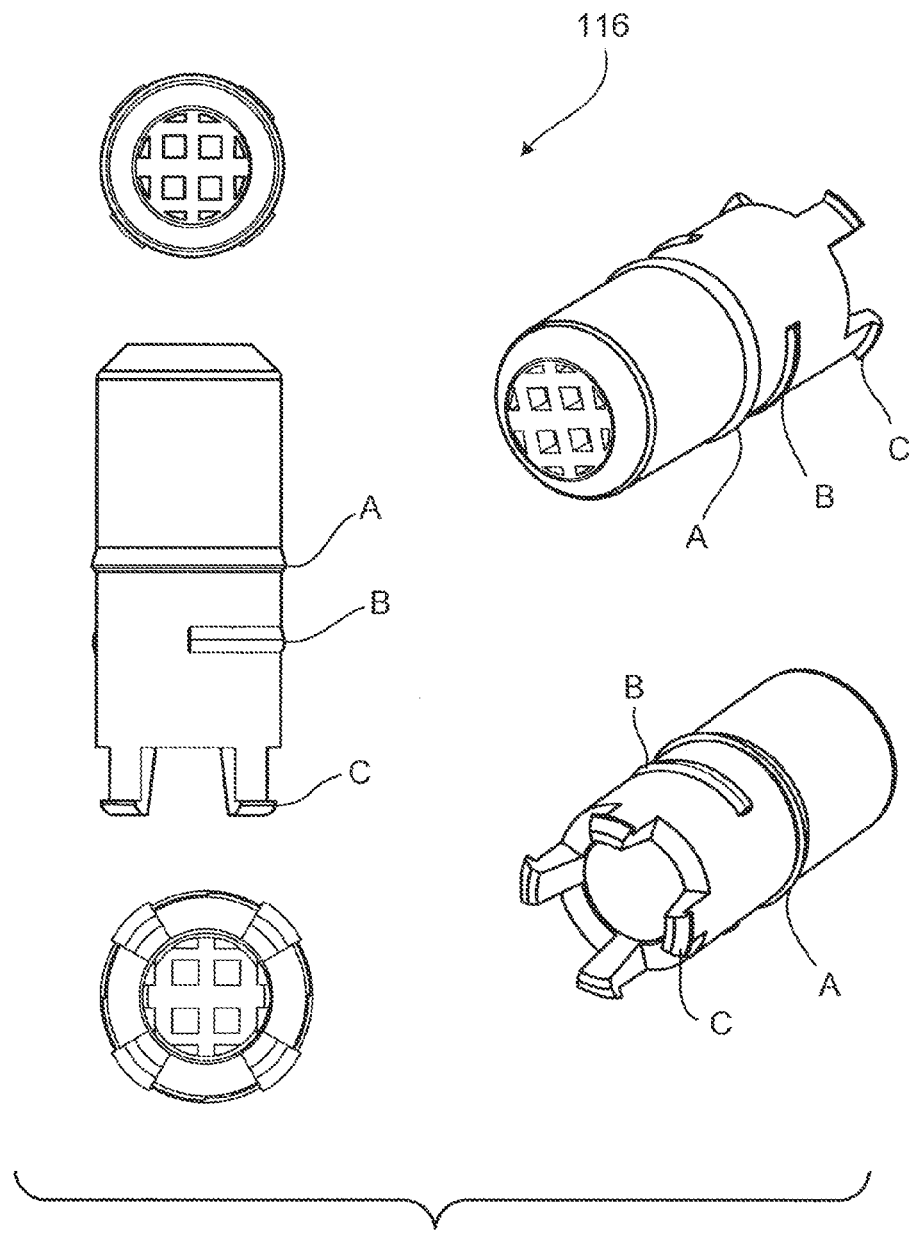
FIG. 6 presents multiple views of an exemplary embodiment of a capsule 116

FIG. 6 presents multiple views of an exemplary embodiment of a capsule 116.

In some of the embodiments described above, the aerosol is generated at a particular point in time or over a small interval of time corresponding to a specific activation step, and/or the aerosol is generated by a user-dependent step. For example, in some cases aerosol generation is associated with one or more inhalation maneuvers by the user. In many of these embodiments, the food product is in a solid state, and may be a substantially dry powder. Our approach, however, is also directed to other series of embodiments, in which the aerosol is generated by a more continuous source, and/or a source external to the user; for example, one or more piezo-electric ultrasonic vibrating disc(s), an air pump, or a compressed air source. Some of these sources may be more appropriate for the generation of aerosols from substantially solid food products, while others may be more appropriate for the generation of aerosols from substantially liquid food products.

In some embodiments the food product is in a substantially liquid state, and aerosol generation by an ultrasound source in communication with the product involves atomization of the liquid in addition to subsequent formation of an aerosol cloud. For example, in some embodiments, the piezo-electric vibrating discs are placed within a liquid food product, and the ultrasonic vibrations of the discs generate an aerosol at the liquid surface.

In many of the embodiments previously described, an aerosol is generated within a housing, mouthpiece, capsule and/or cap, and directly delivered to the user via the housing and/or mouthpiece. In embodiments in which a substantially unconfined aerosol is used (e.g., an aerosol cloud, such as an aerosol cloud generated by an external source, such as an ultrasound source), it may be necessary to generate a highly concentrated aerosol in order to elicit a meaningful taste sensation in the subject. Highly concentrated aerosols, however, have greater rates of collision among particles, and over time, due to inertial impaction, diffusion, etc., the aerosol may become increasingly dilute as it spreads into surrounding air, or particles may coalesce (for example if it is a liquid aerosol). Additional testing may help determine the range of concentrations that would balance taste, aesthetics, and other factors relating to the consumption of substantially unconfined aerosolized food products. Accordingly, in some embodiments, an aerosol cloud may be confined within a pot or other (transparent, opaque, or translucent) medium or container. In a particular embodiment, a closed bubble may be used to confine the aerosol, preserving the aesthetics of a "floating" aerosol (whether it is floating within the container or bubble and/or the container or bubble itself is floating), while maintaining a higher aerosol concentration and enabling a more efficient delivery of the aerosol to the mouth than via open-air "eating" or open-air inhalation. The aerosol bubble or container itself may in some cases be edible. In some cases the bubble or container may open, providing access to the aerosol.

The external source, for example, the ultrasound source, may be placed in some such confining media or containers. In a medium or container that is not completely closed from the outside environment, for example, a pot, the height of the medium or container can be selected to balance the need for protection from convection, diffusion, inertial impaction, and other forces, with the need for access to the aerosol, for example via an open top, via small openings, via openings that can be closed at certain times, etc.

Referring to FIGS. 7A and 7B, a food delivery apparatus 300 includes a container 310 containing a food product 312. A force generator 314 (e.g., an air pump or compressed air source) is attached to the container 310. When activated, the force generator triggers the aerosolization of the food product 312 by passage through an aerosolizing component 316 and subsequent release of the food product 312 into the external environment. The resulting aerosol cloud 318 may then be consumed by, for example, displacement of the cloud or of the subject, or by inhalation.

Figure 8:
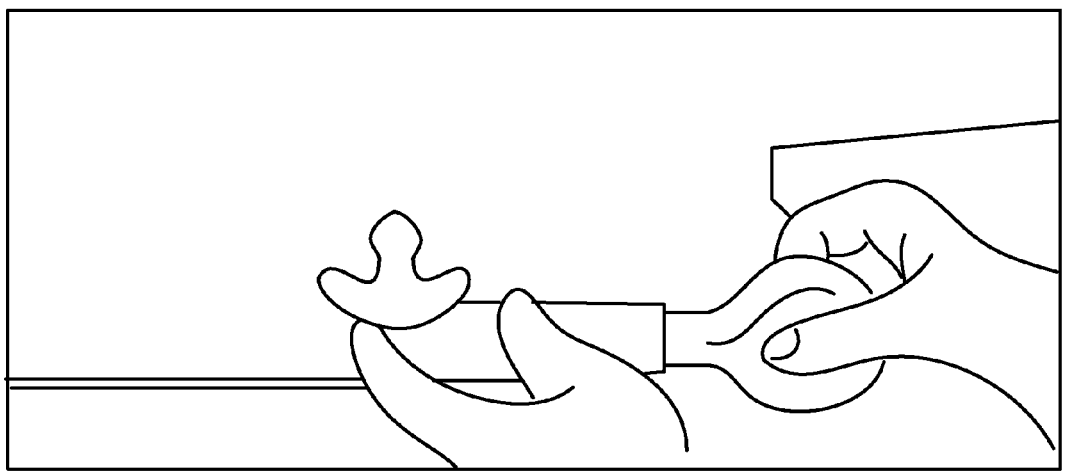
FIG. 8 is a photograph of the aerosolization and release of dehydrated mint particles using a hand-actuated aerosol generating apparatus.
Figure 9A:
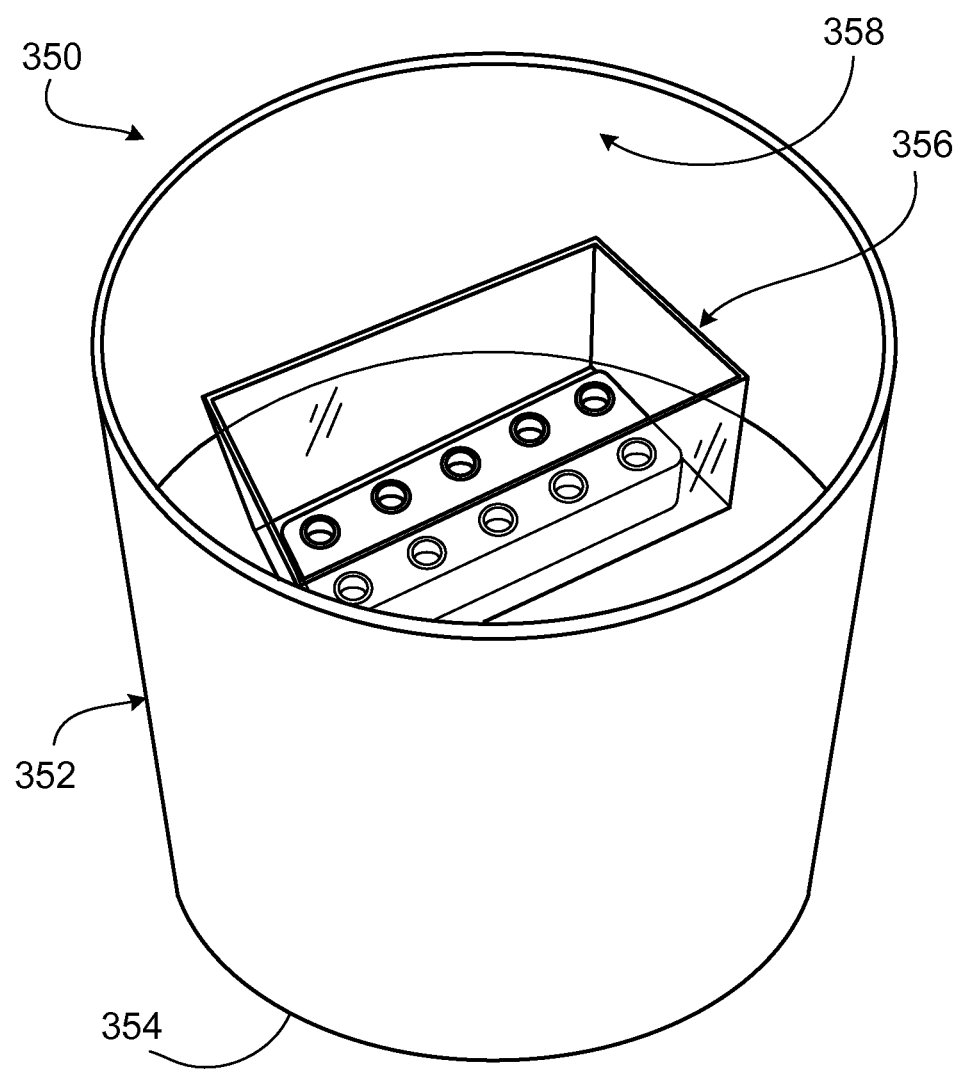
FIGS. 9A-9D are, respectively, a perspective view, a top view, a side view, and a bottom view of a food delivery apparatus.
Figure 9B:
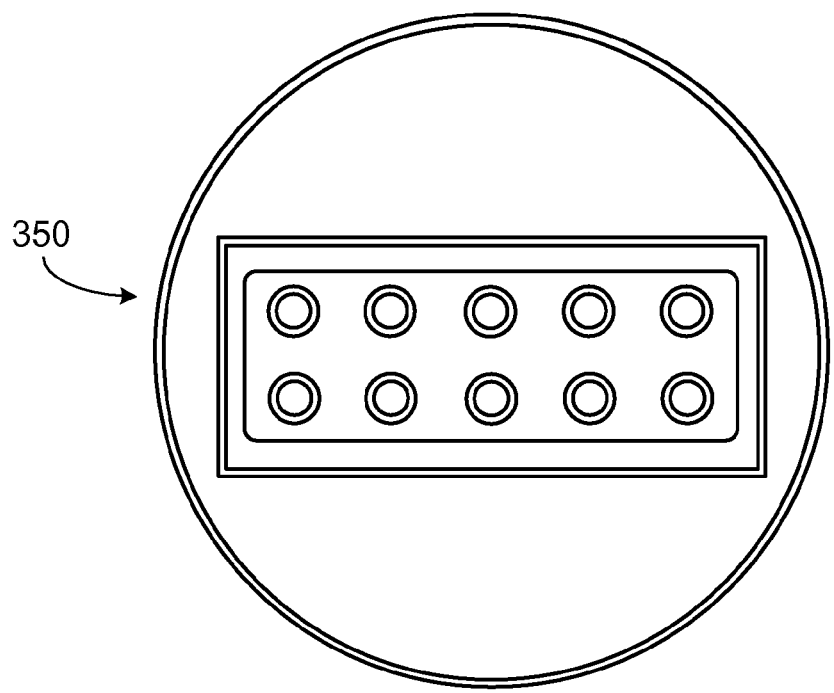
Figure 9C:
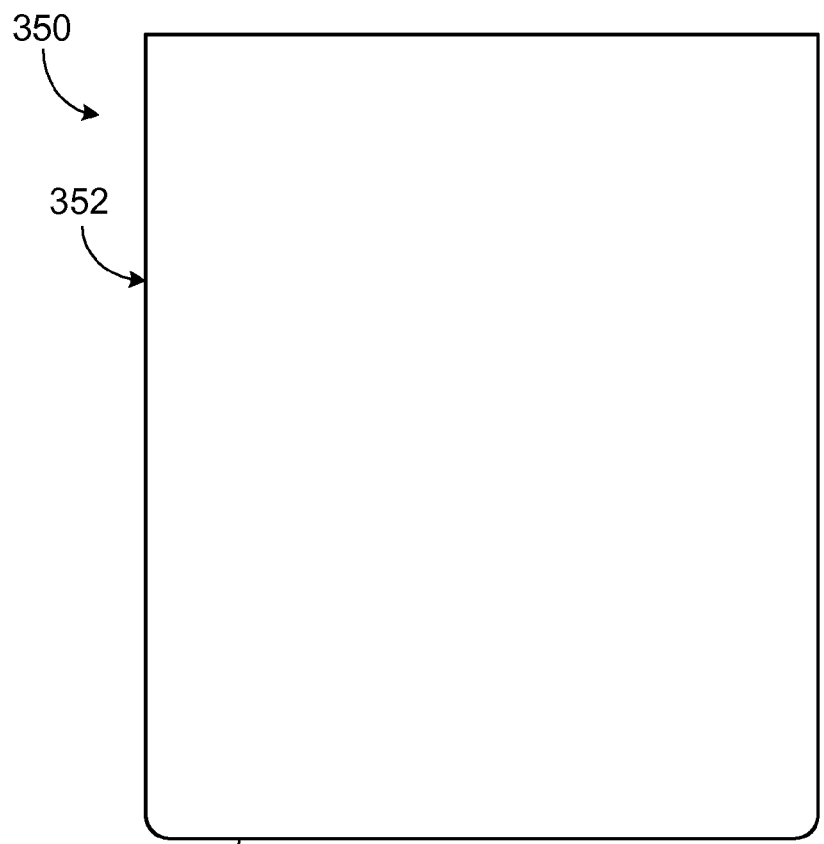
Figure 9D:
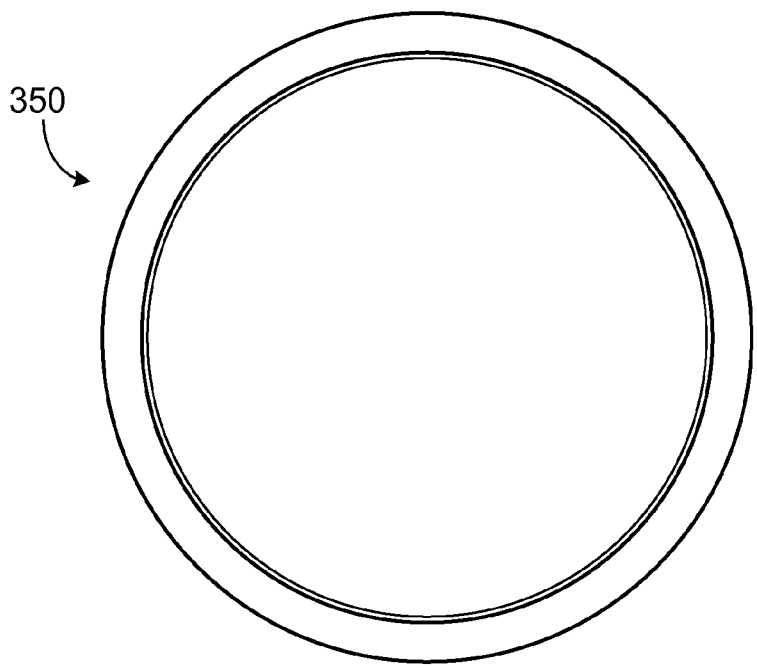
Figure 10A:
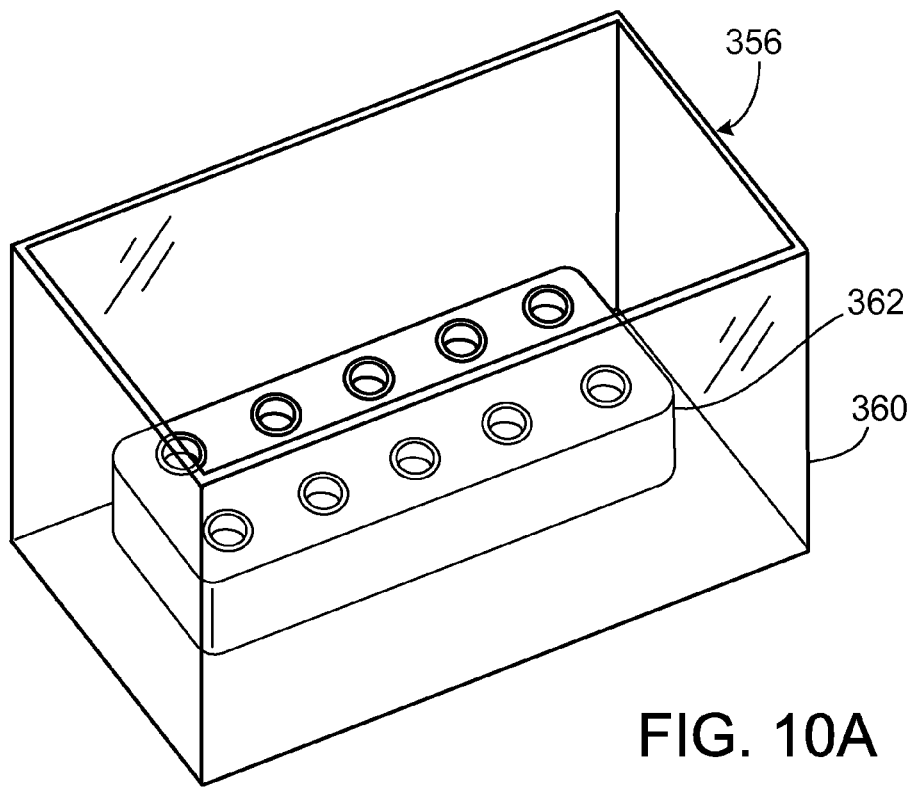
FIGS. 10A-10D are, respectively, perspective, top, side, and end views of an aerosol generating device.
Figure 10B:
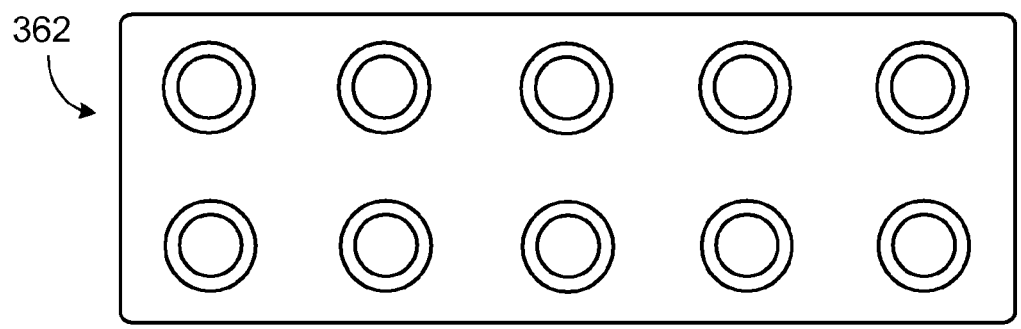
Figure 10C:
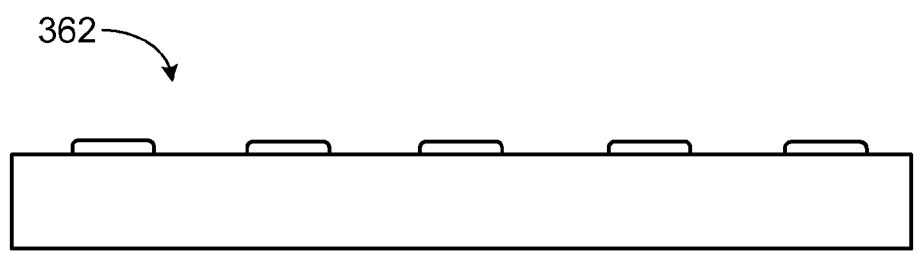
Figure 10D:
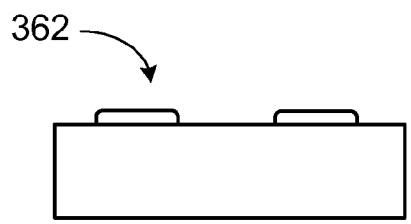

Referring to FIG. 8, a prototype was constructed which included a hand pump as the force generator. The prototype used to aerosolize and release dehydrated mint particles using a hand-actuated aerosol generating apparatus.

Referring to FIGS. 9A-9D, a food delivery apparatus 350 includes a container 352 with a base 354 configured to stably support the container on a supporting surface (e.g., a floor or a table). An aerosol generating device 356 is disposed in an inner cavity 358 of the container 352. The aerosol generating device 356 (shown in more detail in FIGS. 10A-10D) includes a clear plastic case 360 with an open top which receives an aerosol generator 362. The aerosol generator can be, for example, an ultrasonic or a piezoelectric generator.

Figure 11:
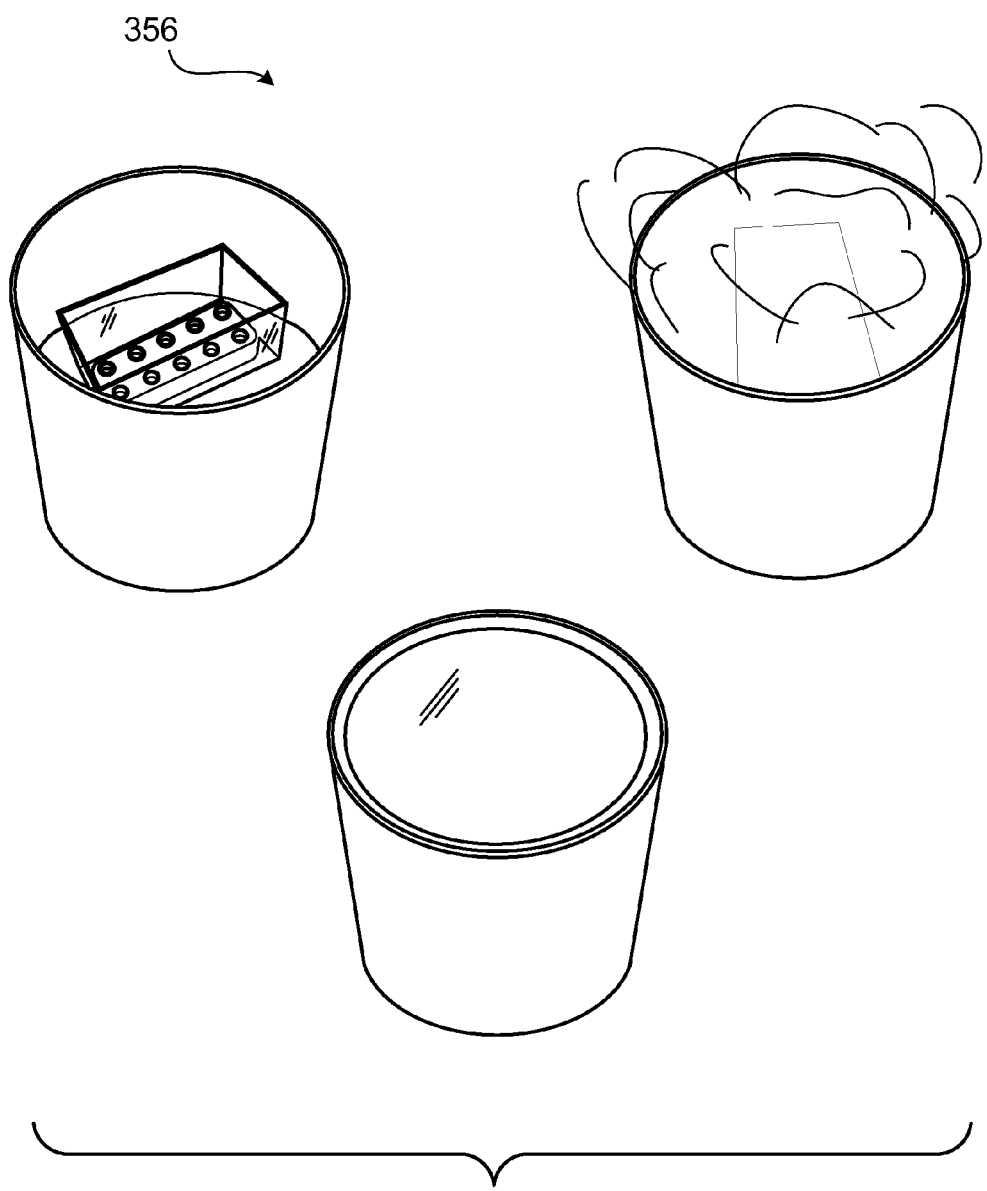
FIG. 11 includes photographs of a food delivery apparatus at different stages of use.
Figure 12A:
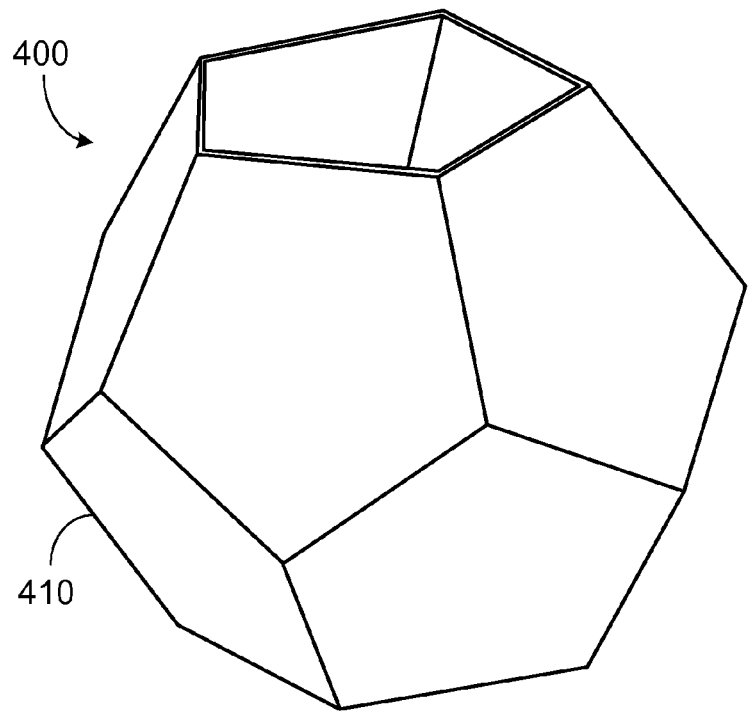
FIGS. 12A-12G are, respectively, perspective, top, front, back, left side, right side and bottom views of a food delivery apparatus.
Figure 12B:
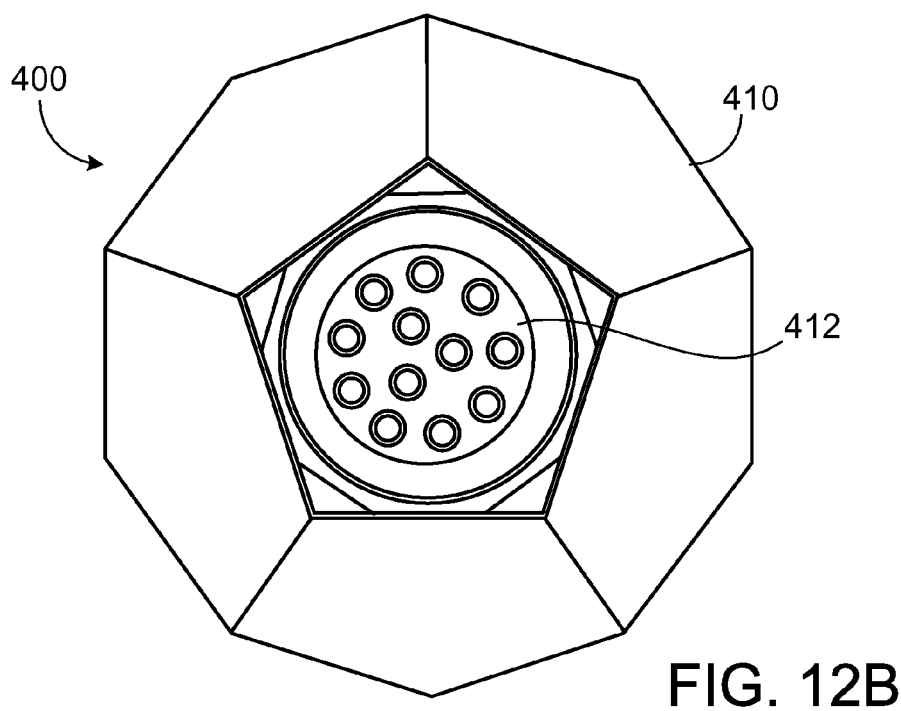
Figure 12C:
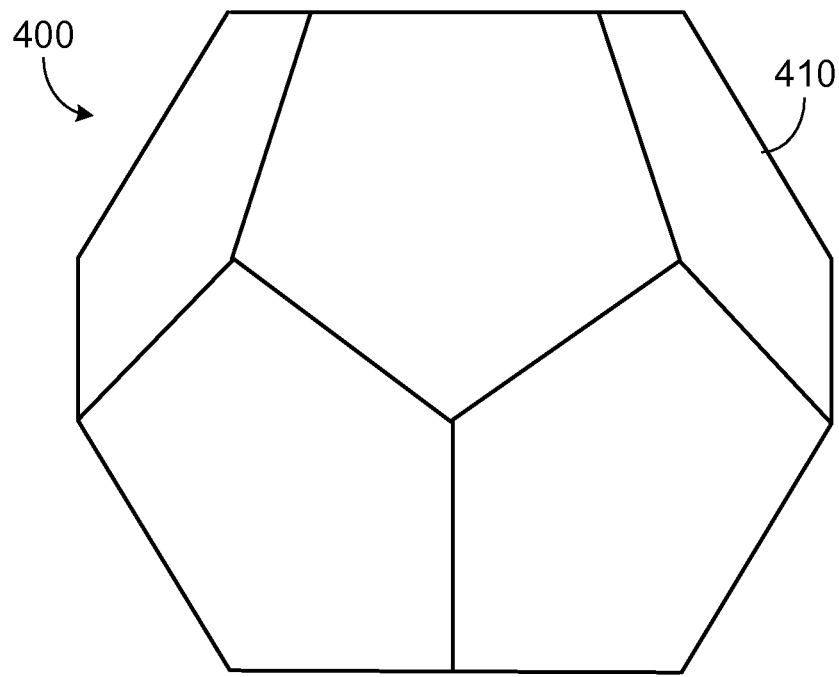
Figure 12D:
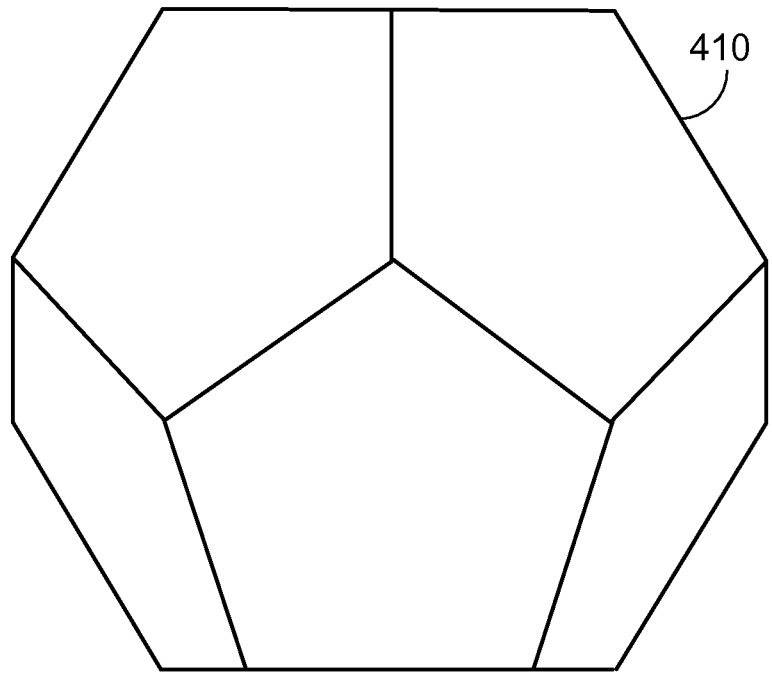
Figure 12E:
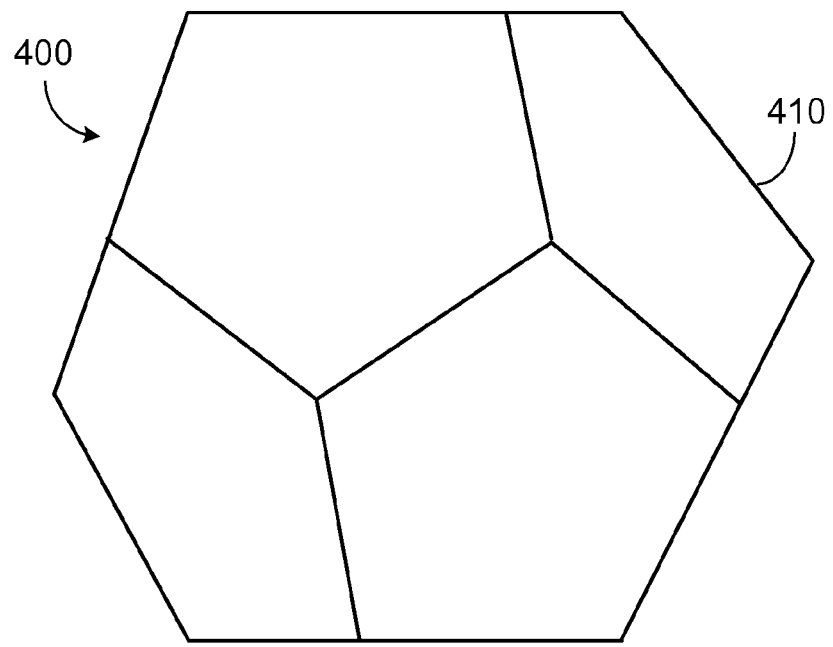
Figure 12F:
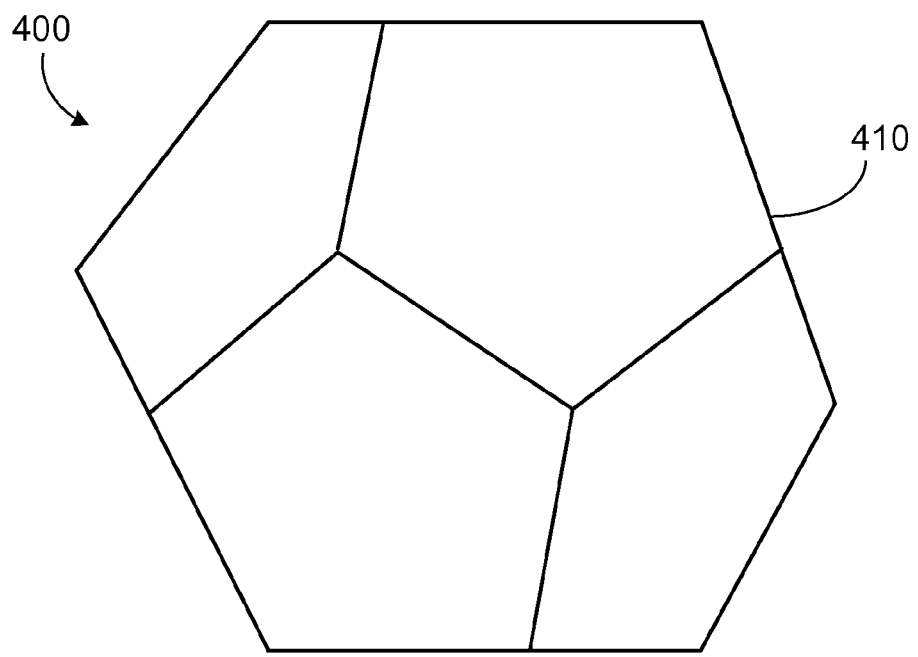
Figure 12G:
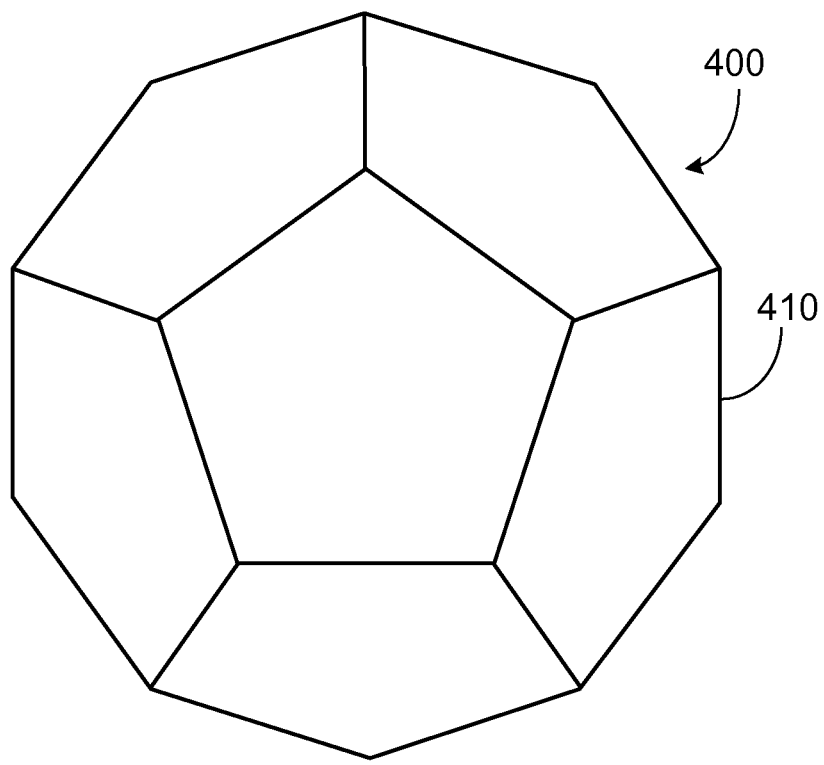

Referring to FIG. 11, a food product can be disposed in the case 360 of the aerosol generating device 356 of a food delivery apparatus 350. When the generator is activated, the food product is aerosolized and, in some cases, passes through the open top of the case 360 of the aerosol generating device 356 into the inner cavity 358 of the container 352. In some cases, the aerosol mixture is sufficiently dense that the aerosol mixture substantially remains within the container 352. The container 352 has an upper opening extending through the container to the interior cavity 358 that is vertically offset from the base when the food delivery apparatus 350 is disposed with the base 354 resting on a supporting surface. In some cases, an upper opening of the container can be closed with a cover.

Figure 14:
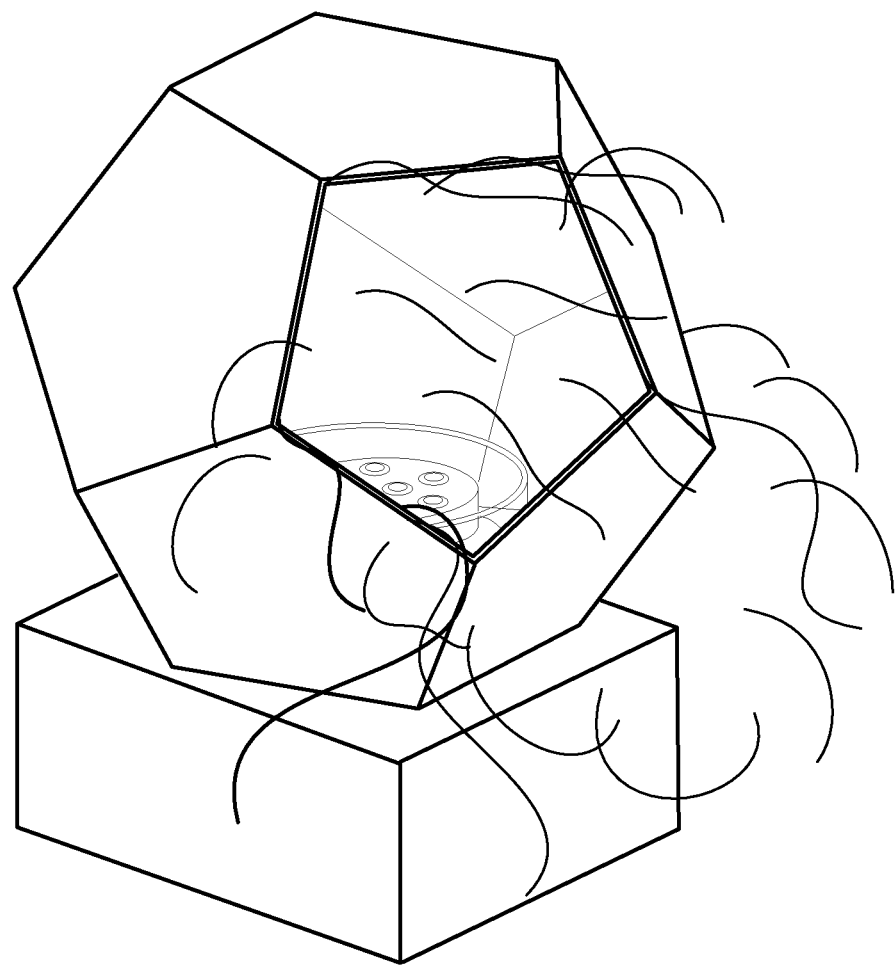
FIG. 14 includes a photograph of a food delivery apparatus in use.

Food delivery apparatuses can be formed with other outer shapes. Referring to FIGS. 12A-12G, a similar food delivery apparatus 400 dodecahedron-shaped container 410 receives an aerosol generating device 412. Referring to FIG. 13, in use, the food delivery apparatus 400 can be disposed with an open face oriented directly upwards. Referring to FIG. 14, in use, the food delivery apparatus 400 can be disposed with an open face oriented upwards at an angle to the supporting surface.

A delivery mechanism can be used to carry the aerosol or portions of the aerosol to a user. In some embodiments, the delivery mechanism consists of a mouthpiece as previously described. Since the aerosol may be generated separately from the delivery device, the delivery device may consist solely of a mouthpiece with airflow-directing elements, which direct the aerosol to surfaces within the mouth upon inhalation as previously described. In some embodiments, it is convenient for the delivery device to be longer, for example to make it easier to access the aerosol without interfering with any aerosol confining structures or devices. In some embodiments, the delivery device is an elongated mouthpiece. In some embodiments, the delivery device is a mouthpiece connected to a separate device that essentially serves to extend the length of the mouthpiece; for example, a hollow cylinder (in some cases, this device may allow a user to use his/her own mouthpiece, while using the same lengthening device as other users; this may be considered a hygienic approach for multiple people to taste the aerosol, without requiring the fabrication of multiple long mouthpieces, which may be costly). In some embodiments, the delivery device is a "food straw".

In some embodiments, the delivery device can be used directly, while in other embodiments, an additional intermediate step can be carried out to further confine smaller portions of the aerosol cloud, after (or during) aerosol generation and before delivery. This arrangement helps increase the proximity of a concentrated portion of the aerosol cloud with the delivery device, improving or possibly making possible detectable and/or appreciable taste. This may also respond in part to hygienic concerns (whether realistic or illusory) about communal use of a single aerosol generating device, by separating the cloud into individual "portions" before consumption.

For example, with a pot or other container in which is an aerosol-generating device (for example an ultrasonic device, within a liquid food product), the aerosol cloud can be collected into smaller containers, such as glasses, champagne flutes, soup ladles, etc., and then a delivery device (for example, a mouthpiece) can be used with the smaller containers. For example, a mouthpiece can be placed within the glass or other container, and by inhalation, the cloud within the glass or container is delivered to the user's mouth. Airflow-directing elements in the mouthpiece would help direct the particles to surfaces within the mouth and limit the extent to which particles could continue further into the respiratory tract.

In certain embodiments of a separate liquid aerosol generating device (e.g., that uses piezo-electric and/or ultrasound sources), typically there are a considerable number of larger drops that reach well beyond the range of the cloud. Thus, attempts to consume the food product from the cloud typically encourage use of a mechanism that allows the consumer to avoid being hit by these drops, for example, by blocking these drops near the source, and/or staying at a distance from the cloud, and/or using a delivery device that minimizes exposure of the consumer to the drops.

Attempts to use gratings over the ultrasound source, with pore sizes smaller than the problematic larger drops, and larger than the cloud droplets, proved unsuccessful. The cloud droplets, though able to fit through the pores, as a whole did not have enough kinetic energy to move easily past the grating to produce a large, dense cloud.

One solution that can be effective is to have some kind of cover above the cloud that prevents the larger drops from projecting out. In some embodiments, this cover concept can be realized by placing a larger cover over the overall container (see, e.g., FIG. 11) that is removed immediately before use. In some embodiments, a separate surface, or a side of the container can extend somewhat over the position of the ultrasound source, thus blocking some projecting drops. In some embodiments, access to the cloud can be via a side opening or space (see, e.g., FIG. 14). In some embodiments, the ultrasound source can be placed at an angle, such that it faces a side of the container, or any non-open portion of the overall device, and thus projects the drops primarily to the corresponding opposite side, rather than out the opening or out an open side (see, e.g., FIG. 13).

Many equivalents to these embodiments are possible, including systems where the container has a variety of dimensions and orientations, and/or where there are covers with various sizes, shapes, and orientations, which may or may not be attached or connected to the rest of the apparatus. Overall, the presence of a solid surface in any form that prevents larger drops from projecting out, located at some distance from the source to allow the cloud to be easily created, is to be considered a variation on the embodiments described herein.

An alternate solution is the use of a delivery device that allows for consumption at a distance. For example, a mouthpiece with airflow-directing elements can be used. In some embodiments, a mouthpiece can be elongated and serve as a "straw", for delivery over a longer distance. In some embodiments, the elongated mouthpiece may consist of two parts—a mouthpiece and an extension piece. For example, the mouthpiece may have airflow-directing elements, and may incorporate a cylinder of a certain diameter and length. The extension piece may, for example, connect with (e.g., fit, snap, screw, etc. into) the mouthpiece, and may have a similar diameter, and be of some length. In this latter system the mouthpieces and the extension pieces may be replaced independently (e.g. each user may have one mouthpiece and, each in turn, use the same extension piece).

Activation of Aerosolization and Delivery of Food Product

The aerosol generating device is any device capable of producing an aerosol of desired characteristics (i.e., particle size, airborne time/suspension duration, emitted dose, etc.). In addition to the aerosol generating device, there may be a delivery device, such as an additional airflow constraining device, a confined space in which the aerosol is contained, an air passage in an inhaler, a mouthpiece, airflow-directing elements, or other devices or structures, that enable, facilitate, or optimize the delivery of the aerosol to the subject's mouth. For example, FIGS. 2A-6 illustrate the capsule and cap, which in many embodiments serve as a food product container and incorporate an aerosol-generating device (consisting primarily of the grating). In many embodiments, the capsule and cap are connected to each other and to a mouthpiece with airflow-directing elements, where the mouthpiece would serve as a delivery device.

By controlling gravitational and inertial forces, the airflow-directing elements found in some embodiments enable delivery of the aerosol cloud substantially to surfaces within the mouth rather than further down the respiratory tract. This aspect of the technology is highly relevant to a number of potential applications of food aerosols. Indeed the same such delivery device can make possible delivery of a wide range of food aerosols, generated in a number of different ways, to a consumer, while minimizing or eliminating coughing and potential interactions with surfaces of the respiratory system beyond the mouth.

The design of any of the devices or structures associated with this technology may also take into consideration and attempt to reduce any tendency to cough, gag, or otherwise react unfavorably to the aerosol.

These devices, and associated devices (such as a food-containing device), can be embodied in a vast number of different ways. The devices described herein are meant to be exemplary.

Triggering the aerosolization of the food product and subsequent delivery of the resulting aerosolized food product may occur by a variety of means including, but not limited to, acts of respiration, device activation, bodily displacement, aerosol displacement and a combination thereof. For example, such acts may include:

a) an act of respiration, for example, by inhalation on a mouthpiece, resulting in exposure of the food product to the aerosol generating device and delivery of the aerosolized food product to the mouth; and/or b) an act of device activation, including, but not limited to, the activation of an ultrasound source, the actuation of a pump, the activation of a compressed air source, the activation of an impeller, the puncturing of a container, the opening of an air passage, that at least in part causes or helps to cause a food product to aerosolize (the aerosol thus formed may be in a substantially confined space (e.g., a spacer), or a substantially open space (e.g., as a "cloud" in air or in a confined structure)); and/or c) an act of respiration directed "on" or "toward" an aerosol (e.g., that is contained in a spacer device, freely floating as a cloud or contained within a larger structure), and that may be facilitated by the use of a straw, mouthpiece, or other apparatus, thereby leading to food deposition substantially in the mouth; and/or d) an act of bodily displacement, such as walking or leaning (possibly in conjunction with a particular placement or positioning of the mouth, tongue, or other body part in a specific way), that exposes a subject's mouth to an aerosol cloud, or portion thereof, thereby leading to food deposition substantially in the mouth, and/or e) an act of aerosol displacement, caused by, for example, an air current, a thermal or pressure gradient, inertial impaction, diffusion, or gravity, that brings an aerosol cloud, or portion thereof, to a position so as to expose a subject's mouth to the aerosol cloud, thereby leading to food deposition substantially in the mouth (even where aerosol displacement results in dilution of the particle concentration and spreading out the cloud); and/or f) an additional act of device activation, device use, space constraining, airflow confinement, etc., or of placement or positioning of the mouth, lips, tongue, jaw, head, or other body part in a particular configuration, shape, etc.; or other additional action that helps produce the proper aerosolization and/or delivery and/or tasting of the food product (e.g., use of a food straw, opening/closing of a containing chamber, lifting of the tongue to divert airflow, etc.). Such acts may be used to help reduce a tendency to cough, gag, or otherwise react unfavorably to the food product.

All references to a powder, liquid, aerosol, cloud, etc. made herein may equivalently refer to some fraction or portion of the total amount of the powder, liquid, aerosol, cloud, etc.

The device itself may be designed for single use (for example, disposable) or multiuse, for example, where the dosage capsule is replaced or the dosage chamber refilled. Alternatively, or in addition, parts of the device, for example, the mouthpiece, the food-containing apparatus, the capsule, and/or the cap, may be disposable. In some embodiments, the device may incorporate a force-generating mechanism, such as a pump or compressed air source, to aerosolize the food product. In some embodiments, the device may incorporate a propellant.

In some embodiments, the device may be designed for "single action", "repeated action", or "continuous action" aerosolization and/or delivery, depending on whether it is intended to aerosolize and/or deliver the product in a single, short-term step (e.g., one inhalation on an inhalation-triggered apparatus), in multiple discrete steps (e.g., multiple inhalations on an inhalation-triggered apparatus), or over a longer-term continuous step (e.g., maintaining an aerosol cloud in open air), where "step" can refer to any combination of simultaneous and/or sequential processes by which the device aerosolizes and/or delivers the product. Many factors, including whether the device is intended for use by one subject or multiple subjects at a time, will help determine which of these step sequences (if any) is appropriate for any particular embodiment.

The device might also include additions, such as spacers, lights, valves, etc., to enhance the visual effect and/or the control over the aerosol and/or dosage. These additions may also enhance the experience of inhaling the aerosols.

In some embodiments, the body of the entire apparatus, or parts of the apparatus, could be manufactured of an edible/ingestible substance, such as a cookie, cracker, chocolate, or sugar product, etc. This would allow the device to be enjoyed either during the aerosol delivery or afterwards, thus enhancing the overall experience.

In some embodiments, the device may be similar to an inhaler or inhalation device, such as a dry powder inhaler (DPI) or metered dose inhaler (MDI); a "pot" that holds an ultrasound source and confines somewhat the aerosol cloud produced by the source; a "fountain" that ejects and/or circulates the aerosol; a hand-held pump device; a compressed air device; a food straw device; a multi-person, communal device; a tabletop device. A variety of materials may be used to form the device, or parts thereof, including: plastics (e.g. polycarbonates, which are relatively strong, polypropylene, acrylonitrile butadiene styrene, polyethylene, etc.), various metals, glass, cardboard, rigid paper, etc.

In some embodiments, the aerosolized food product should be of sufficient size to limit entry into the respiratory tract but of small enough size to allow for suspension in the air. In some embodiments, particle size may be a manufacturing requirement of pre-atomized, generally solid food products, for example the food products placed inside the capsule/cap of certain embodiments, or certain dry food products used in association with an air pump or compressed air source. In some embodiments, particle size may be a requirement of the aerosol-generating device, for (generally liquid) food products that are only atomized upon aerosol generation, for example the food products used in association with ultrasound sources to produce an aerosol cloud.

In some embodiments, the mean size of the aerosolized food product is at least 1, 2, 3, 4, 5, 10, 15, 20, 25, 30, 35, 40, 45, 50, 55, 60, 70, 75, 80, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 325, 350, 375, 400, 425, 450, 475, or 500 microns. In some embodiments, the mean size of the aerosolized food product is less than 500, 450, 400, 350, 325, 300, 275, 250, 245, 240, 235, 230, 225, 220, 215, 210, 205, 200, 195, 190, 185, 180, 175, 150, 140, 130, 120, 110, 100, 90, 80, 70, 60, 50, 40, 30, 20, or 10 microns in size. Ranges intermediate to the above recited amounts, e.g., about 50 microns to about 215 microns, are also intended to be part of this invention. For example, ranges of values using a combination of any of the above recited values as upper and/or lower limits are intended to be included.

Especially, but not exclusively, in some embodiments in which intake is by inhalation, minimum particle size is an important feature of the approach. The food aerosol particles are designed to be substantially delivered and deposited into the mouth, for example by the forces of gravity or inertial impaction, but to not be easily delivered and deposited substantially further into the respiratory tract, for example the trachea or lungs. Such food particles would thus possess a size larger than that which focuses penetration into the lungs (i.e., larger than about 10 microns). For example, breath-activated inhaler-like devices, such as the devices shown (in part or in whole) in FIGS. 5-17, generate an aerosol that would fairly easily follow the inhaled air toward the lungs were it not for the aerosol particles' larger size (and the delivery device's airflow-directing elements).

Especially, but not exclusively, in embodiments in which intake is by displacement of the subject or of the aerosol (e.g., with an aerosol cloud), maximum particle size is an important feature of the approach. Indeed, the aerosol cloud must remain suspended in air for at least a brief time so that displacement into the mouth can occur. Thus the particles must not be so large such that they rapidly settle from the air. This will greatly depend on the force(s) and/or mechanism(s) by which the particles are held in the air (e.g., by "natural" forces alone, such as inertia, diffusion, etc., or by additional forces, such as an impeller, air currents, convection, etc.). Accordingly, in some embodiments, the particles should be less than about 500 microns under typical suspension forces and mechanisms. For example, ultrasound sources in liquid food products can produce a standing aerosol cloud that, so long as convection is minimal, balances gravity, diffusion, inertial impaction, and other forces, to stay suspended in the air.

The specific parameters of the apparatus and intake method will in part determine whether the subject is "inhaling" or "eating" when intake of the aerosol occurs. This generally corresponds to (1) whether the aerosol is entering the subject's mouth and/or throat via inhaled air (physiologically, while the epiglottis is directing the air into the trachea toward the lungs) or whether the aerosol is entering the subject's mouth by another method (such as displacement of the aerosol or of the subject), and (2) whether the subject's expectation is that the aerosol is a kind of food to be (eventually) swallowed (physiologically, while the epiglottis is blocking passage to the trachea). In any case, it should be further noted that the food product, after deposition in the mouth, may be eventually swallowed and consumed essentially as any other typical food product.

In some embodiments of devices in which an aerosol is generated by inhalation, e.g. the devices shown in FIGS. 5, 6, and 20, relatively dry, solid food powders of appropriate size can be used as the food product. Preliminary tests have shown that the water-solubility of the dry powders used plays a role in the taste and potential coughing reflex resulting from intake of the aerosolized food product. Powders of particles that tend to be more rapidly water-soluble, such as ground chocolate bars, or certain chocolate-based powders, give rise to a generally pleasing reaction upon contact of the particles with the tongue and other surfaces within the mouth. In the case of ground chocolate bars, for example, the effect is in some cases similar to that of sensing chocolate melt very rapidly in one's mouth. Particles that are less water-soluble, such as certain ground-cocoa-based powder products, tend to be considered harsher and more likely to elicit less pleasurable reactions, such as a dry-mouth sensation or coughing. However, in some instances, a combination of both kinds of powders, in varying proportions, provides interesting flavor complexity.

In some embodiments in which a liquid aerosol is generated, such as in the devices illustrated in FIGS. 9A-14, the aerosol generation and delivery devices are constrained by the need to have sufficient aerosol quantity and/or concentration to elicit a meaningful taste sensation. Thus in some embodiments, the density of the aerosol cloud, and the quantity of aerosol consumed in one inhalation or other single delivery step, must be above a minimum threshold, depending on the user's sensibility to taste, the food product, and many other conditions.

In some embodiments in which a liquid aerosol is generated, for example, with ultrasound sources in liquid food product, particles suspended in the liquid (for example if the liquid is colloidal) must be generally smaller than the size of the aerosol particles that are to be generated for the source to efficiently produce an aerosol. In addition, in some embodiments with liquid aerosols, for example some embodiments with ultrasound sources in liquid food product, surfactants cannot play a critical role in producing the desired taste (which is the case, according to preliminary tests, of wine) since the aerosolization separates the surfactants from the rest of the food product, giving rise to a greater proportion of surfactants in the liquid, and thus a greater proportion of other food components in the cloud (e.g., in the case of wine, more acidic substances) that distort the true flavor of the food product.

Food Products, Including Aerosol Powders

By designing a food form that can be aerosolized (particles much larger than 500 microns fall quickly out of the air unless supported by an external force) and yet has sufficiently large particles (greater than approximately 1, 2, 3, 4, 5, 10, 15 or 20 microns) such that few or no particles enter the lungs on inspiration, our technology results in deposition and delivery into the mouth. Ideally, the particles would be designed (sized) such that, for example, at least about 50%, at least about 60%, at least about 70%, at least about 80%, at least about 90%, at least about 95%, at least about 97%, or at least about 99% of the particles deposit in the mouth and do not extend further into the respiratory tract. The design of the particles should also take into consideration reducing any tendency to cough, gag, or otherwise react unfavorably to the aerosol.

Dry powder particles can be created through a number of different methods. Initially, the food product may be dehydrated. Alternatively or in addition, where the food is a more malleable or liquid based food, the food may be frozen first to facilitate subsequent grinding or chopping. The food product may subsequently be ground to form food particles of the appropriate size. Grinding of the food products can be performed by use of a mortar and pestle. Alternatively or in addition, food products may be chopped, for example using a mechanical or electrical grinder, knives, etc. The resulting ground or chopped food particles can subsequently be filtered through sieves (for example by hand, using an electrical or mechanical sieve shaker, by an air classification system, by a screening system, etc.) to achieve the appropriate particle size. Another approach is to use a powder mill that grinds down larger particles into pre-defined sizes. Spray drying, in which a mixture of water and the material to be dried is forced through a nozzle into a high-temperature drum, instantly evaporating the water droplets clinging to the material, may also be utilized. These methods, in addition to others, would allow for the creation of specifically sized particles capable of being aerosolized, but large enough not to pass easily through the mouth and throat and continue into the respiratory tract.

These dry powder particles could be created from a single food or ingredient, such as chocolate, coffee, or truffles, or from a combination of foods or ingredients, such as combinations representative of an entire dish or meal (e.g., mixed fruits or meat and potatoes). In the case of chocolate, chocolate bars, chocolate powder, cocoa powder, and other forms and varieties of foods derived from the cocoa plant may be used. In addition, in some cases, spices and other (natural or artificial) flavorings may be used alone or in combination with such food ingredients to create other tastes or sensations (e.g., natural or artificial chocolate, raspberry, mango, mint, vanilla, cinnamon, caramel, and/or coffee flavors). In some implementations, the aerosolizable food product comprises at least two different foods that exhibit contrasting reactivity. Additionally, the apparatus may contain a single dose of food product or multiple doses/portions of the food product. In addition, they may be made from largely liquid products, for example by extracting dissolved solids or using other solid components. In some embodiments, flavors can be experienced while using less of the actual product compared to normal ingestion. In addition, by mixing different powders, new flavors can be created.

The food aerosol may also be a liquid that is aerosolized, for example by an ultrasound source that is in communication with a liquid food product; or by a "spray" mechanism, similar to those for liquids and gases in spray cans ("aerosol cans") or vaporizers. Such liquids may be prepared by a variety of processes such that they are or include a concentrate, additive, extract, or other form of a food product that in some way preserves or enhances, and can deliver, a taste.

A liquid aerosol may also be generated by an ultrasonic device, such as vibrating piezo-electric discs placed within a container of liquid food product.

Depending on the food product(s) and device(s) used, the food product may be stored and/or contained in the form of a tablet or pill, in a blister pack, within a capsule, as simply a powder in a jar-like container, and/or in a tray, box, container, thermos, bottle, etc.

In some embodiments, it is possible to deliver odors using appropriately designed and appropriately sized particles, which may be utilized independently or in addition to embodiments described herein, i.e., in addition to delivery of aerosolized food product so as to enhance the aesthetic experience.

Please note that "food product", "aerosol", "particle", and other similar terms are used throughout this document, and though they may typically refer to small solid particles derived from foods, these terms may in some cases refer to any of the other food-derived products described herein.

Other Potential Properties of the Aerosols

Humidity or other ambient atmospheric conditions, which may vary over time and/or space, can be used to trigger time- or location-dependent changes in the aerosol and/or in the sensory detection and transduction it initiates in the subject(s). These conditional triggers may lead the particles to take on different gustatory, olfactory, aerodynamic, chemical, physical, geometric, and/or other properties, which in turn may alter the taste, texture, color, size, aerosolizability, and/or other aspect of the particles.

The purpose of such conditional triggers is generally to create a more interesting and dynamic experience for the subject(s). The trigger may depend on reaching a threshold atmospheric condition (e.g., greater than 50% humidity), or a threshold associated with the subject. The atmospheric condition may change the aerosol particles themselves and/or may allow them to interact differently with the subject's sensory mechanisms. For example, in low-humidity air, an aerosol may take on one chemical/physical state, which gives it a first taste, and in high-humidity air, it may take on a different chemical/physical state, which gives it a second taste. As another example, an aerosolized aerosol may have initially no taste and/or odor, or an initial taste and/or odor reminiscent of a certain food product (which may, for example, be detected initially by a subject through the olfactory system, before intake of the aerosol through the mouth); and after the aerosol is taken through the mouth, the ambient environment of the mouth may trigger a change in the aerosol that gives it a taste and/or odor, or new taste and/or odor reminiscent of a different food product. Over time but while the food product is still in the mouth, it may continue to evolve, evoking different sensations for the subject. Mechanisms like these could be used to create the impression of sequentially eating different courses of a meal, such as an appetizer followed by a main course followed by dessert.

Time Airborne/Suspension Time

Depending on the particular embodiment, the food product can be in aerosol form (airborne) for different durations. For example, in the case of an inhaler-based device, the food product typically remains airborne only for the time over which inhalation and intake occur, which may be, for example, up to about ½ second, up to about 1 second, up to about 3 seconds, up to about 5 seconds, up to about 8 seconds, up to about 10 seconds, up to about 15 seconds, or possibly greater time periods. Alternatively, where the food delivery device operates by producing an aerosol cloud, the food product may remain suspended in the air for, for example, at least about 1, 2, 3, 4, 5, 6, 7, 8, 9, 10, 15, 20, 25, 30 or 60 seconds, or at least about 2, 5, 10, 15, 20, 30, 45, 60, 90, 120, or 180 minutes. Mechanical agitation of the aerosol cloud, for example, by convection, can serve to increase the time during which the aerosol cloud is suspended.

Applications

Our apparatus can transform how food is experienced, allowing for an enhanced aesthetic experience of food. For example, the apparatus can allow subjects to experience food by exposing themselves to, for example, rooms filled with food clouds, immersive chambers and food straws. Indeed, businesses, restaurants and nightclubs could provide such "food experiences".

In some embodiments, our technology can allow subjects to experience food by exposing themselves to aerosolized food via individual, hand-held, and/or portable devices. In some embodiments, our technology may be used in and/or associated with social contexts similar to candy eating or cigarette smoking. For example, some embodiments may be carried about and used at various points throughout the day, or used simultaneously by multiple users.

In various other embodiments, the technology can allow multiple subjects to have a communal experience while appreciating food aerosols, for example in embodiments in which a single aerosol-generating device is associated to multiple delivery devices, such as a pot-like container confining a liquid aerosol cloud that is delivered by breath actuation to multiple subjects each using independent mouthpiece devices with airflow-directing elements.

In addition, the apparatus can serve to provide nutrition to subjects either who are incapable of chewing or for whom delivery of food is not convenient. For example, the food delivery apparatus may be useful for elderly or young children, for whom chewing or feeding is inconvenient. In addition, individuals with medical conditions that require them to be fed in particular ways (e.g., by a feeding tube or intravenously) may use certain embodiments of this invention as a way to experience and taste food again.

The apparatus can also serve to facilitate the intake of medication that may not be of a pleasurable taste. If used in conjunction with delivery of the medication, e.g. orally, the apparatus can provide an additional flavor that masks the flavor of the medication.

Alternatively, the proposed food delivery apparatus may be used for weight control or addiction mitigation applications. For example, the food delivery apparatus can allow for subjects to consume relatively small or negligible quantities of food products or certain unhealthy or addictive substances, and the exposure to the food particles via the apparatus may provide a sensation or satisfaction normally associated with the consumption of a larger quantity of the food or substance in question, thereby potentially satisfying hunger or addictive urges without the (potentially negative) consequences of actually consuming larger amounts of the substance(s). Indeed, the food delivery apparatus may form a basis for dieting, weight control and healthy eating programs (for example, by satisfying cravings for sweets, fatty foods, chocolate and caffeine) and addiction treatment (for example, by satisfying urges for alcohol, smoking, drugs but in much smaller, less harmful amounts).

In addition, the food delivery apparatus may be used to improve quality of life, for example, with respect to individuals subject to special dietary restrictions. For example, the food delivery apparatus may allow individuals who suffer from allergies (e.g., gluten allergy) or other conditions (e.g., lactose intolerance) that normally prevent them from consuming specific products to consume relatively small or negligible quantities of these products without triggering an allergic or physical reaction, while possibly providing a sensation or satisfaction normally associated with the consumption of a larger quantity of the food or substance in question.

Additionally, the food delivery apparatus can serve as a means for taste-testing a number of items in a simple and efficient way. For example, a patron at a restaurant can taste test various dishes on the menu before making a selection. Additionally, chefs may use the food delivery apparatus to test combinations of foods while cooking or designing a recipe. Similarly, the apparatus may serve as an aid in cooking lessons, as an international "dining" experience for a subject, as a way to teach children about food, etc.

Other useful applications of the food delivery apparatus include, but are not limited to hunger relief (e.g., in the emergency conditions of a famine) and for animal feedings.

EXEMPLIFICATION OF THE INVENTION

The following example is expected to be illustrative of the invention and in no way limits the scope of the invention.

Example 1

To help determine an ideal particle size for food aerosolization from a single-actuation dry powder inhaler, mint powder samples, with approximate initial mean particle sizes of at least 140 microns, were utilized. A mortar and pestle was used to grind the dry mint powder. Mean particle size was reduced to as low as ~11 microns, as determined using a HELOS-RODOS particle sizing system. Particles of different sizes were placed in separate size 3 capsules and tested in a handheld inhaler.

Results

Tests were made with samples of mint particles with approximate mean particle sizes of 140, 111, 72, 40, 18, and 11 microns. Capsules (each containing approximately 30-120 mg of mint) were placed in the aerosolizer and punctured, and the inhaler was actuated to release the particles into the air. A large fraction of the particles could be seen to fall within 5 seconds after release, though this fraction decreased with decreasing sample particle size. It was relatively high in tests with approximate mean particle sizes of 140, 111, and 72 microns, and relatively low in tests with approximate mean particle sizes of 40, 18, and 11 microns. Tests with approximate mean particle sizes of 18 and 11 microns produced fairly mist-like and uniform plumes, with fewer visually distinct particles.

Figure 15:
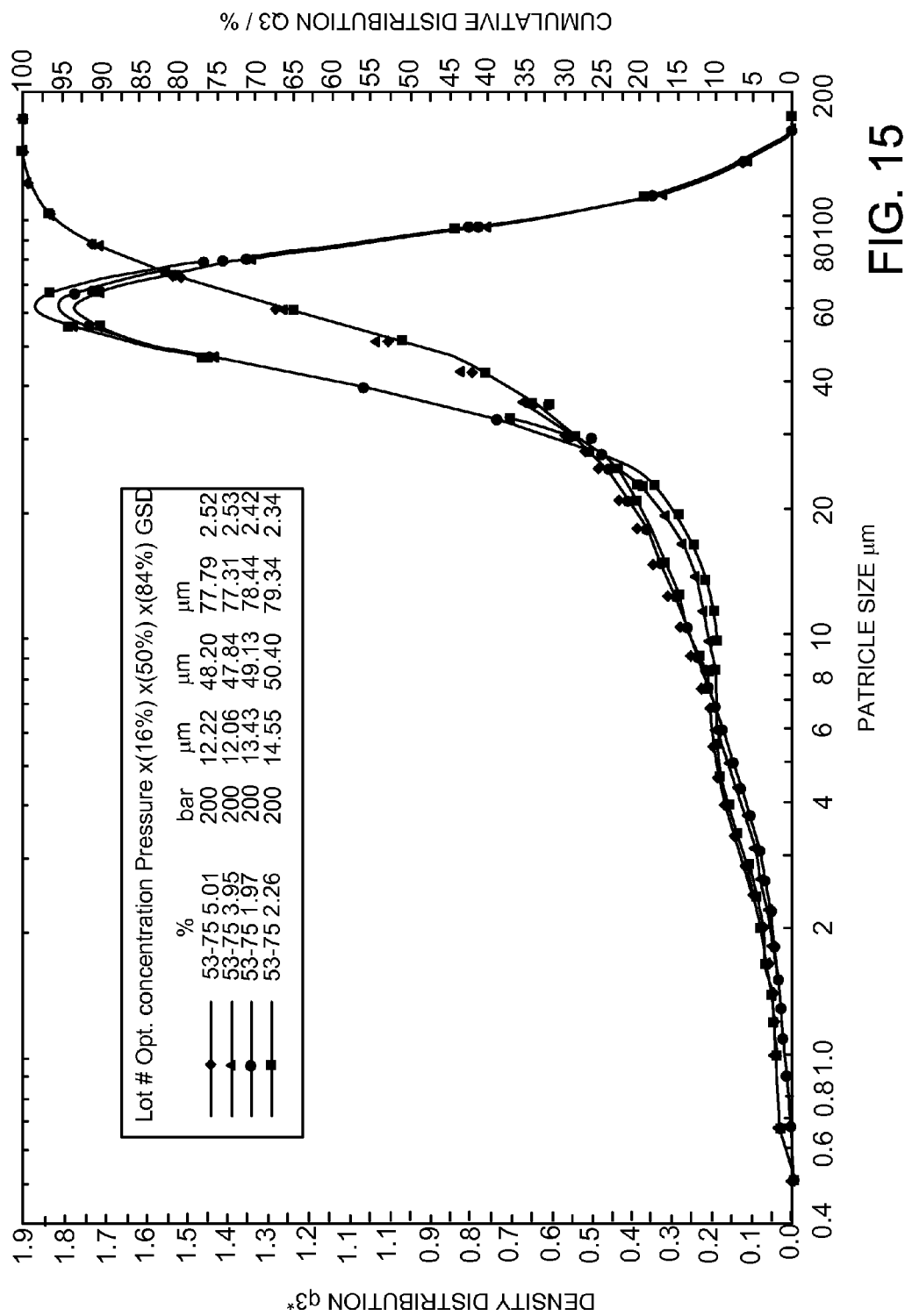
FIG. 15 is a graph from a HELOS-RODOS particle size analysis of dried, crushed, and sieved mint leaves.

FIG. 15 shows the density distribution and cumulative distribution for four trials from the same sample. These data show that, for this particular sample, roughly 87% of the particles are larger than about 10 microns, and that roughly 79% of the particles are larger than about 20 microns. These findings demonstrate that a dehydrated food product (mint leaves) can be made into aerosolized particles substantially of a size (e.g. between at least 18 and 70 microns) that would typically deposit into the mouth upon inhalation.

In a sample of particles whose mean is approximately in this range, a small or negligible fraction of particles is able to enter into the throat and lungs and yet a considerable fraction of particles remains suspended for at least 5 seconds after a single inhaler actuation.

Clearly larger particle sizes could be aerosolized for at least as long with a larger aerosolization force or a more continued force of aerosolization, such as a continually or intermittently operating fan.

Example 2

Figure 17A:
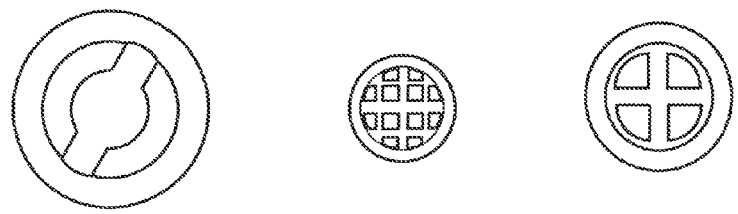
Figure 17B:
Figure 17C:
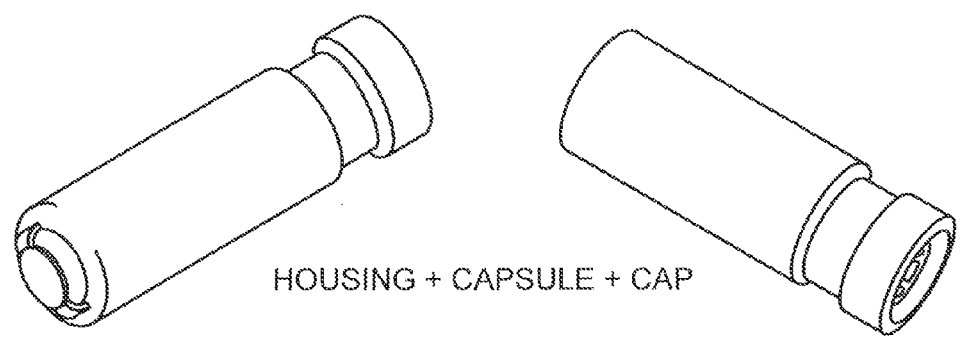

An aerosolized food delivery device as depicted in FIGS. 16-18 was designed so as to deliver aerosolized chocolate. Chocolate was chopped into fine particles, which was subsequently screened by size. It was found that many readily available chocolates, when ground, remain dry enough to aerosolize in the delivery device described so long as care is taken not to handle the particles excessively, which causes them to quickly melt and fuse. The dryness of commercially available chocolate or cocoa powders makes such powders useful in producing a different aerosol taste experience, while enabling the powders to be far more stable (e.g. far less prone to melting). Using sieves, particular size ranges can be selected, and it was found that (likely among other size ranges), samples with a large number of particles with diameters roughly in the range of 125-180 microns are appropriate for strong taste and aerosolizability. It was also found that certain particles, even though of a size that should fall out of the air before reaching the deeper respiratory system (>10 microns), can cause a coughing reflex, even when of sizes reaching on the order of 100 microns or larger, but this is noticeably reduced with the airflow-directing mouthpiece element. (It was also found that the water-solubility of the particles might play a role in the likelihood of eliciting a coughing reflex.) Particles substantially larger than 180 microns are increasingly difficult to aerosolize and begin to taste like small pieces of chocolate simply dropped onto the tongue.

To simplify the filling procedure, it was determined that standard size 3 and size 4 capsules contain amounts of the chocolate powder appropriate for a single-inhalation "dose". A standard manual capsule filling machine can thus be used to prepare a large number of such doses for transfer to the powder compartment of the delivery device.

What is claimed is:

1. A delivery apparatus comprising:
   an aerosol delivery device for discharge of aerosolized particles sized between 10-500 microns; the aerosol delivery device including:
   a mouthpiece defining a fluid flow passage extending between an inlet to an outlet;
   a deflection member spaced apart from a plane of the outlet of the mouthpiece, and positioned outside the mouthpiece, the deflection member including a flat surface generally perpendicular to an axis of the mouthpiece and in opposition to the airflow direction in the mouthpiece the flat surface opposing flow of particles along the axis of the mouthpiece, the deflection member has an outer dimension defining an outer perimeter that is at least roughly equal to an external dimension of the mouthpiece; and
   two bridges extending from the outlet of the mouthpiece to the deflection member outer perimeter spacing the deflection member outward from the outlet of the mouthpiece;
   the deflection member configured to redirect aerosolizable particles exiting the outlet of the mouthpiece toward sides of a user's mouth.

2. The delivery apparatus of claim 1, further comprising a reservoir containing aerosolizable particles sized between 10-500 microns.

3. The delivery apparatus of 2, wherein the reservoir is configured to be replaceable.

4. The delivery apparatus of claim 2, wherein the reservoir is integral with the mouthpiece.

5. The delivery apparatus of claim 2, wherein the reservoir comprises an edible portion.

6. The delivery apparatus of claim 1, wherein the aerosol delivery device includes an end cap attached to the mouthpiece and defining at least one air intake passage extending through the end cap.

7. The delivery apparatus of claim 6, wherein the end cap and the mouthpiece together define an interior cavity sized to receive a capsule containing particles.

8. The delivery apparatus of claim 1, further comprising a replaceable capsule containing particles.

9. The delivery apparatus of claim 1, wherein the mouthpiece is in fluid communication with an aerosol generating device.

10. The delivery apparatus of claim 1, wherein the aerosol delivery device comprises an airflow passage defined by the mouthpiece.

11. The delivery apparatus of claim 1, wherein the aerosolizable particles comprise at least two different foods that exhibit contrasting reactivity.

12. The delivery apparatus of claim 1, wherein the aerosol delivery device comprises an edible portion.

13. The delivery apparatus of claim 1, further comprising an activating device configured to emit a dose per activation of between about 5 milligrams and 100 milligrams.

14. The delivery apparatus of claim 1, wherein the apparatus is handheld.

15. The delivery apparatus of claim 1, wherein the apparatus is a tabletop or freestanding unit.

16. The delivery apparatus of claim 1, wherein the deflection member is generally perpendicular to the axis of the outlet of the mouthpiece.

17. The delivery apparatus of claim 1, wherein the two bridges are on opposite sides of the deflection member.

18. The delivery apparatus of claim 1, wherein the deflection member is circular and the two bridges are diametrically opposed to each other.

19. The delivery device of claim 1, wherein the flat surface redirects aerosolized particles exiting the outlet of the mouthpiece in a first direction perpendicular to the axis of the mouthpiece, a second direction opposed to the first direction, a third direction perpendicular to both the first direction and the axis of the mouthpiece, and a fourth direction opposed to the third direction.

20. The delivery apparatus of claim 1, further comprising a reservoir containing aerosolizable particles.

21. The delivery apparatus of 20, wherein the reservoir is configured to be replaceable.

22. The delivery apparatus of claim 20, wherein the reservoir is integral with the mouthpiece.

23. A method of delivering particles sized between 10-500 microns, the method comprising:
aerosolizing particles;
moving the aerosolized particles along a flow passage, toward an outlet of a mouthpiece that includes, a deflection member having an outer dimension defining an outer perimeter that is at least roughly equal to an external dimension of the mouthpiece, the deflection member spaced apart from a plane of the outlet of the mouthpiece by two bridges extending from the outlet of the mouthpiece to the deflection member outer perimeter spacing the deflection member outward from the outlet of the mouthpiece, the deflection member including a flat surface generally perpendicular to an axis of the mouthpiece and in opposition to the airflow direction in the mouthpiece, the flat surface opposing flow of aerosolized particles along the axis of the mouthpiece and redirecting the aerosolized particles exiting the outlet of the mouthpiece to sides of the user's mouth; and
depositing at least a portion of the aerosolized particles in a user's mouth.

24. The method of claim 23, wherein aerosolizing the particles comprises passing airflow generated by inhalation through an air intake passage, a compartment containing a particles, and the mouthpiece.

25. The method of claim 23, wherein aerosolizing the particles comprises inhaling on the mouthpiece.

26. The method of claim 25, wherein inhaling on the mouthpiece exposes the particles to an aerosol generating device.

27. The method of claim 23, wherein the deflection member is circular and the two bridges are diametrically opposed to each other.

28. A delivery apparatus comprising:
an aerosol delivery device for discharge of aerosolized particles sized between 10-500 microns; the aerosol delivery device including:
a mouthpiece defining a fluid flow passage extending between an inlet to an outlet; and
a deflection member having an outer dimension defining an outer perimeter that is at least roughly equal to an external dimension of the mouthpiece, the deflection member spaced apart from a plane of the outlet of the mouthpiece by two bridges extending from the outlet of the mouthpiece to the deflection member outer perimeter spacing the deflection member outward from the outlet of the mouthpiece, the deflection member including a flat surface generally perpendicular to an axis of the mouthpiece and in opposition to the airflow direction in the mouthpiece the flat surface opposing flow of particles along the axis of the mouthpiece;
the deflection member configured to redirect aerosolizable particles exiting the outlet of the mouthpiece toward sides of a user's mouth.

29. The delivery apparatus of claim 28, wherein the aerosol delivery device includes an end cap attached to the mouthpiece and defining at least one air intake passage extending through the end cap.

30. The delivery apparatus of claim 29, wherein the end cap and the mouthpiece together define an interior cavity sized to receive a capsule containing particles.

31. The delivery apparatus of claim 28, further comprising a replaceable capsule containing particles.

32. The delivery apparatus of claim 28, wherein the mouthpiece is in fluid communication with an aerosol generating device.

33. The delivery apparatus of claim 28, wherein the aerosol delivery device comprises an airflow passage defined by the mouthpiece.

34. The delivery apparatus of claim 28, wherein the aerosolizable particles comprise at least two different foods that exhibit contrasting reactivity.

35. The delivery apparatus of claim 28, wherein the aerosol delivery device comprises an edible portion.

36. The delivery apparatus of claim 28, further comprising an activating device configured to emit a dose per activation of between about 5 milligrams and 100 milligrams.

37. The delivery apparatus of claim 28, wherein the apparatus is handheld.

38. The delivery apparatus of claim 28, wherein the apparatus is a tabletop or freestanding unit.

39. The delivery apparatus of claim 28, wherein the two bridges are on opposite sides of the deflection member.

40. The delivery apparatus of claim 39, wherein the deflection member is circular and the two bridges are diametrically opposed to each other.

41. The delivery apparatus of claim 39, wherein the reservoir comprises an edible portion.

* * * * *